(12) United States Patent
Goel et al.

US008956817B2

(10) Patent No.: US 8,956,817 B2
(45) Date of Patent: Feb. 17, 2015

(54) IDENTIFICATION OF MICRORNAS (MIRNAS) IN FECAL SAMPLES AS BIOMARKERS FOR GASTROENTEROLOGICAL CANCERS

(75) Inventors: Ajay Goel, Dallas, TX (US); C. Richard Boland, Dallas, TX (US); Alexander Link, Dallas, TX (US); Francesc Balaguer, Dallas, TX (US)

(73) Assignee: Baylor Research Institute, Dallas, TX (US)

(*) Notice: Subject to any disclaimer, the term of this patent is extended or adjusted under 35 U.S.C. 154(b) by 1151 days.

(21) Appl. No.: 12/901,467

(22) Filed: Oct. 8, 2010

(65) Prior Publication Data

US 2011/0086353 A1    Apr. 14, 2011

Related U.S. Application Data

(60) Provisional application No. 61/250,388, filed on Oct. 9, 2009, provisional application No. 61/294,030, filed on Jan. 11, 2010.

(51) Int. Cl.
*C12Q 1/68* (2006.01)
*C12P 19/34* (2006.01)

(52) U.S. Cl.
CPC ............ *C12P 19/34* (2013.01); *C12Q 1/6806* (2013.01); *C12Q 1/6886* (2013.01); *C12Q 2600/158* (2013.01); *C12Q 2600/178* (2013.01)
USPC .......................... 435/6.12; 435/91.2; 536/25.4

(58) Field of Classification Search
USPC ................................ 435/6.12, 91.2; 536/25.4
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 6,586,177 B1 | 7/2003 | Shuber | |
| 6,645,730 B2 | 11/2003 | Nair | |
| 7,252,955 B2 | 8/2007 | Pant et al. | |
| 7,312,053 B2 * | 12/2007 | Tada et al. ............... | 435/91.2 |
| 2007/0202511 A1 | 8/2007 | Chen et al. | |
| 2008/0045418 A1 | 2/2008 | Xia | |
| 2009/0099034 A1 | 4/2009 | Ahlquist et al. | |
| 2010/0075304 A1 * | 3/2010 | Raponi et al. ................ | 435/6 |
| 2011/0318742 A1 * | 12/2011 | Sung et al. ................ | 435/6.11 |

FOREIGN PATENT DOCUMENTS

WO    2009/015357    * 1/2009

OTHER PUBLICATIONS

Chan, Jennifer A., et al., "MicroRNA-21 is an Antiapoptotic Factor in Human Glioblastoma Cells," Cancer Res., Jul. 15, 2005, 65:(14) 6029-6033.

Chen, Xi, et al., "Characterization of MicroRNAs in serum: A Novel Class of Biomarkers for Diagnosis of Cancer and other Diseases," Cell Research, (2008), 18:997-1066.
Chen, Caifu, et al., "Real-Time Quantification of MicroRNAs by Stem-Loop RT-PCR," Nucleic Acids Research, (2005), vol. 33, No. 20, 9 pages.
Du, Pan, et al., "Lumi: A Pipeline for Processing Illumine Microarray," Bioinformatics, vol. 24, No. 13, (2008), pp. 1547-1548.
Graser, A., et al., "Comparison of CT Colonography, Colonoscopy, Sigmoidoscopy and Faecal Occult Blood Tests for the Detection of Advanced Adenoma in an Average Risk Population," Gut, (2009), 58:241-248.
Hui, Angela, et al., "Robust Global Micro-RNA Profiling with Formalin-Fixed Paraffin-Embedded Beast Cancer Tissues," Laboratory Investigation, (2009), 89, pp. 597-606.
Hunter, Melissa Piper, et al., "Detection of MicroRNA Expression in Human Peripheral Blood Microvesicles," PLOS One, Nov. 2008, vol. 3, Issue 11, 11 pages.
Imperiale, Thomas F., et al., "Fecal DNA Versus Fecal Occult Blood for Colorectal-Cancer Screening in an Average-Risk Population," The New England Journal of Medicine, Dec. 23, 2004, 351:2704-2714.
International Search Report for PCT/US2010/052112, dated Jun. 7, 2011, 4 pages.
Levine, Joel S., et al., "Adenomatous Polyps of the Colon," The New England Journal of Medicine, (2006), 355:2551-2557.
Lu, Jun, et al., "MicroRNA Expression Profiles Classify Human Cancers," Nature, vol. 435, Jun. 9, 2005, pp. 834-838.
Mandel, Jack S., et al., "Reducing Mortality from Colorectal Cancer by Screening for Fecal Occult Blood," vol. 328, No. 19, May 13, 1993, pp. 1365-1371.
Meissner, Helen I., et al., "Patterns of Colorectal Cancer Screening Uptake Among Men and Women in the United States," Cancer Epidemiol Biomarkers, (2006), 15:389-394.
Mestdagh, Pieter, et al., "A Novel and Universal Method for MicroRNA RT-qPCR Data Normalization," http://genomebiology.com/2009/10/6/R64, Genome Biology 2009, vol. 10, Issue 6, Article R64, 10 pages.
Mitchell, Patrick S., et al., "Circulating MicroRNAs as Stable Blood-Based Markers for Cancer Detection," PNAS, vol. 105, No. 30, Jul. 29, 2008, pp. 10513-10518.
Motoyama, Kazuo, et al., "Over-and Under-Expressed MicroRNAs in Human Colorectal Cancer," International Journal of Oncology, (2009), 34:1069-1075.

(Continued)

*Primary Examiner* — Kenneth Horlick
(74) *Attorney, Agent, or Firm* — Hunton & Williams LLP

(57) ABSTRACT

A simple, rapid, inexpensive, and promising commercial biomarker assay method for multiple diseases is described herein. The present invention detects miRNA-based biomarkers in human stool specimens. The method of the present invention amplifies miRNA directly from stool specimens without any prior miRNA extraction. Differential expression of specific microRNAs in stool of colorectal cancer CRC and adenoma patients suggest fecal microRNAs as a novel potential biomarker for colorectal neoplasia detection. The method of the present invention has diagnostic, prognostic, and therapeutic relevance for gastroenterological cancers/colorectal cancer and as well as further acquired or hereditary GI diseases.

21 Claims, 12 Drawing Sheets

(56) References Cited

OTHER PUBLICATIONS

Nagasaka, Takeshi, et al., "Analysis of Fecal DNA Methylation to Detect Gastrointestinal Neoplasia," J. Natl Cancer Inst., vol. 101, Issue 18, Sep. 16, 2009, pp. 1244-1258.

Ng, Eko, et al., "Differential Expression of MicroRNAs in Plasma of Patients with Colorectal Cancer: A Potential Marker for Colorectal Cancer Screening," Gut, (2009), 58:1375-1381.

Ouyang, Daniel L., et al., "Noninvasive Testing for Colorectal Cancer: A Review," American Journal of Gastroenterology, (2005), 100(6):1393-1403.

Rabinowits, Guilherme, et al., "Exosomal MicroRNA: A Diagnostic Marker for Lung Cancer," Clinical Lung Cancer, vol. 10, No. 1, Jan. 2009, pp. 42-46.

Schetter, Aaron J., et al., "MicroRNA Expression Profiles Associated with Prognosis and Therapeutic Outcome in Colon Adenocarcinoma," American Medical Association, vol. 299, No. 4, Jan. 30, 2008, pp. 425-436.

Siegel, Rebecca, et al., "Cancer Statistics," CA Cancer J. Clin., (2007);57;43-66.

Vandesompele, Jo, et al., "Accurate Normalization of Real-Time Quantitative RT-PCR Data by Geometric Averaging of Multiple Internal Control Genes," Genome Biology, (2002), 12 pages.

Zou, Hongzhi, et al., "High Detection Rates of Colorectal Neoplasia by Stool DNA Testing with a Novel Digital Melt Curve Assay," Gastroenterology, (2009), 136:459-470.

\* cited by examiner

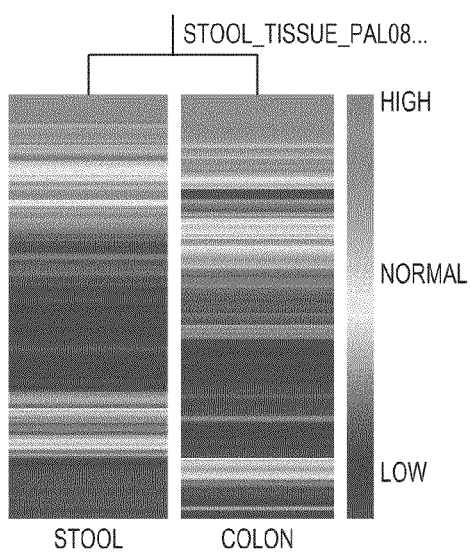
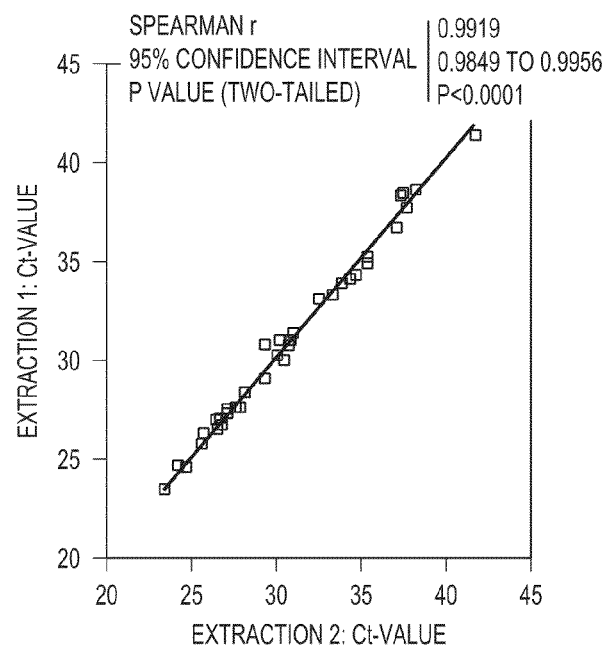
FIG. 8A
FIG. 8B
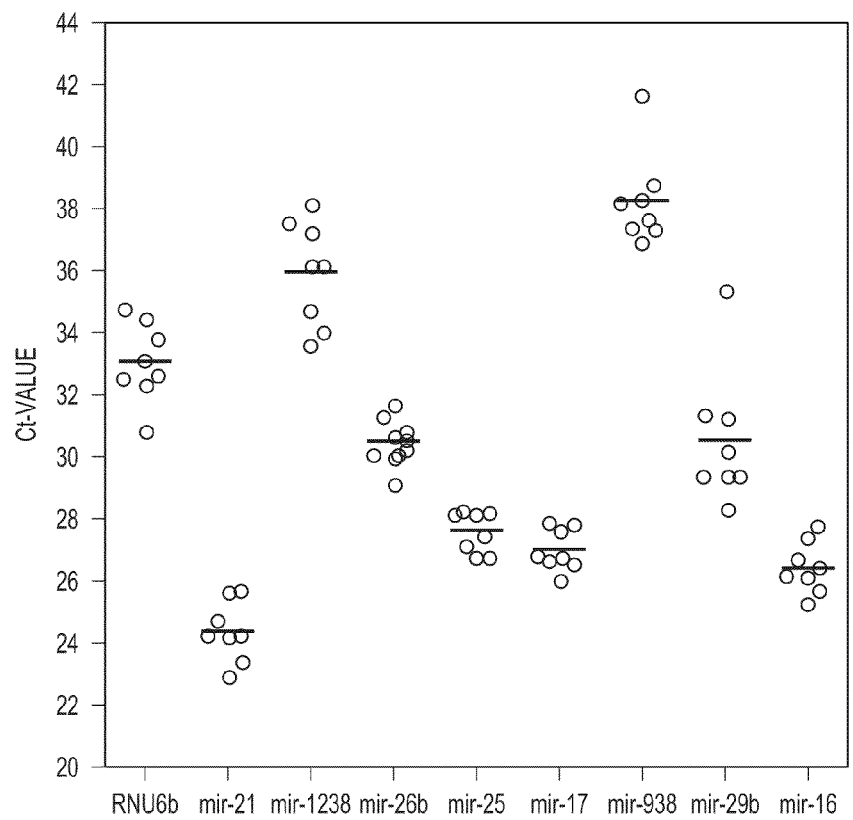
FIG. 8C

IDENTIFICATION OF MICRORNAS (MIRNAS) IN FECAL SAMPLES AS BIOMARKERS FOR GASTROENTEROLOGICAL CANCERS

CROSS-REFERENCE TO RELATED APPLICATIONS

This application claims priority to U.S. Provisional Patent Application Ser. No. 61/250,388, filed Oct. 9, 2009, and U.S. Provisional Patent Application Ser. No. 61/294,030, filed Jan. 11, 2010, the entire contents of which are incorporated herein by reference.

STATEMENT OF FEDERALLY FUNDED RESEARCH

This invention was made with U.S. Government support under Contract Nos. R01 CA072851 and R01 CA129286 awarded by the National Cancer Institute, National Institutes of Health (NIH). The government has certain rights in this invention.

TECHNICAL FIELD OF THE INVENTION

The present invention relates in general to the field of noninvasive biomarkers, and more particularly, to the detection of miRNA-based biomarkers in human stool specimens for the diagnosis of hereditary and acquired gastrointestinal disorders and specifically gastroenterological cancers including colorectal cancers.

BACKGROUND OF THE INVENTION

Without limiting the scope of the invention, its background is described in connection with biomarkers for colon and gastroenterological cancer detection.

U.S. Pat. No. 7,252,955 issued to Pant et al. (2007) discloses an immunological assay and kit for colon cancer screening. Fecal glycoproteins are extracted from individual samples such that immunogenicity is maintained. The purified fecal glycoproteins are reacted with antibodies to Colon and Ovarian Tumor Antigen (COTA). The mucin antigen COTA is specifically present in colorectal cancer tissue and not in normal colons. The amount of COTA in the fecal sample is determined and used to indicate the presence of colon cancer.

U.S. Pat. No 6,645,730 issued to Nair (2003) (hereinafter the '730 patent) describes a method for isolating viable, biologically substantially pure exfoliated fecal colonocytes at normal ambient temperature. According to the '730 patent, immunocoprocytes and inflammatory cells indicative of certain gastrointestinal conditions and a noninvasive method for detecting colorectal cancer are set forth. Composition of transport and suspension media for isolation of colonocytes are detailed.

U.S. Pat. No. 6,586,177 issued to Shuber (2003) provides methods for detecting disease by analysis of a patient sample to determine the integrity of nucleic acids in the sample. According to the invention the method determines the presence of cancer or precancer, the method comprising the steps of: determining an amount of nucleic acid, using an assay that detects both wild-type and mutant nucleic acid, in a patient sample comprising shed cells or cellular debris. The cancer is selected from lung cancer, esophageal cancer, prostate cancer, stomach cancer, colon cancer, pancreatic cancer, liver cancer, and lymphoma. The sample obtained from the patient comprises stool, sputum, pancreatic fluid, bile, lymph, blood, urine, cerebrospinal fluid, seminal fluid, saliva, breast nipple aspirate, and pus.

SUMMARY OF THE INVENTION

Colorectal cancer (CRC) is the second leading cause of cancer-related deaths in the United States. Although screening can reduce cancer-related mortality, the non-invasive screening programs have only achieved a modest decrease in mortality. MicroRNAs (miRNAs) play important roles in a wide array of biological processes regulating gene expression. Expression pattern of miRNAs is commonly dysregulated in neoplasia and unique miRNA expression pattern allows discrimination between various types of cancers. Since their discovery, miRNAs have shown be excellent biomarkers, and their potential as a tool for cancer screening is a subject of excitement. The present invention describes the use of fecal miRNAs as novel biomarkers for colorectal neoplasia screening The present inventors efficiently extracted miRNAS from stool specimens using a novel modified protocol. Data from independent studies showed high reproducibility for miRNA extraction and expression. miRNA expression patterns were similar in stool specimens among healthy volunteers and reproducible in stool samples that were collected serially in time from the same individuals. miRNA expression profiles from 29 patients demonstrated higher expression of miR-21 and -106a in patients with adenomas and CRCs, compared with individuals free of colorectal neoplasia. Data obtained by the present inventors indicate that miRNAs can be extracted from stool easily and reproducibly. The stools of patients with colorectal neoplasms have unique and identifiable patterns of miRNA expression, suggesting fecal miRNAs as an excellent candidate for the development of a non-invasive screening test for colorectal neoplasms.

The present invention further relates to a method for the isolation and detection of miRNA-based biomarkers in human stool specimens; and, for the diagnosis of gastroenterological and colorectal cancers. The method of the present invention describes the amplification of miRNA directly from stool specimens without any prior miRNA extraction, so called direct miRNA analysis (DMA). Total RNA was extracted from feces with Qiagen miRNAeasy Mini Kit using modified protocol. Total RNA concentration was measured using spectrophotometer and Ribogreen RNA quantitation kit. Illumina microRNA microarray was performed to evaluate the difference in microRNA expression patterns between normal colonic mucosa tissues arid stool samples of healthy subjects. Quantitative RT-PCR was used to measure the microRNA expression in stool samples. Differences in miR-NAs expression were studied in 8 healthy volunteers. The inventors also performed miRNA expression analysis in stool (Fecal Occult Blood Test) samples of 29 patients with normal colonic mucosa, adenoma and CRC's.

One embodiment the present invention describes a method for isolating and amplifying one or more miRNAs from a stool sample comprising the steps of: (i) mixing the stool sample with a solution of a salt, RNAse free water or both to form a suspension, (ii) centrifuging the suspension, (iii) separating a supernatant from the centrifuged suspension, (iv) measuring a total RNA/miRNA concentration in the supernatant using a spectrophotometer, (v) transcribing a cDNA from the total RNA using one or more specific miRNA primers, and (vi) amplifying the transcribed cDNA using a polymerase chain reaction assay to obtain the one or more amplified miRNA.

In one aspect of the present invention the salt is an ionic salt selected from the group comprising of sodium salts, potassium salts, calcium salts, magnesium salts, ammonium salts, iron salts and quarternary ammonium salts. In specific aspects the salt is sodium chloride (NaCl) and the biological sample to the salt solution ratio is 1:10. In an other aspect the biological sample to the salt solution ratio is 1:1, 1:2, 1:5, 1:10, 1:25, 1:50, 1:100, 1:500 and 1:1000.

In another embodiment the present invention is a method of detecting a disease in a subject suspected of having a disease comprising the steps of, obtaining a stool sample from the subject, mixing the stool sample with a solution of a salt, RNase free water, or both to form a suspension, centrifuging the suspension, separating a supernatant from the centrifuged suspension, measuring a total RNA/miRNA concentration in the supernatant using a spectrophotometer, transcribing a cDNA from the total RNA using one or more specific miRNA primers, amplifying the transcribed cDNA using a polymerase chain reaction assay to obtain one or more amplified miRNAs, and comparing the levels of the one or more miRNAs from the stool samples of the subject suspected of having the cancer with that of one or more healthy subjects, wherein a change in the level of expression of the one or more miRNAs indicates the presence of the cancer.

In specific aspects of the method of the present invention the disease is a cancer or a gastroenterological disease and the biological sample is a stool sample. In another aspect the RNase free water is water free from any RNase activity—specifically filtered or purified. In one aspect the salt is an ionic salt selected from the group consisting of sodium salts, potassium salts, calcium salts, magnesium salts, ammonium salts, iron salts and quarternary ammonium salts. In another aspect the ionic salt is sodium chloride (NaCl). In another aspect the biological sample to the solution ratio is 1:10. The biological sample to the solution ratio is 1:1, 1:2, 1:5, 1:10, 1:25, 1:50, 1:100, 1:500, and 1:1000.

In yet another embodiment the present invention is a method of isolating and amplifying one or more miRNAs from a stool sample comprising the steps of: (i) mixing the stool sample with a sodium chloride solution, RNase free water or both to form a suspension, wherein the stool sample to sodium chloride solution ratio is 1:10, (ii) centrifuging the suspension, (iii) separating a supernatant from the centrifuged suspension, (iv) measuring a total RNA/miRNA concentration in the supernatant using a spectrophotometer, (v) transcribing a cDNA from the total RNA using one or more specific miRNA primers, and (vi) amplifying the transcribed cDNA using a polymerase chain reaction assay to obtain the one or more amplified miRNAs from the stool sample.

In one embodiment the present invention further describes a method of detecting a colorectal or a gastroenterological cancer in one or more subjects comprising the steps of: obtaining a stool sample from the one or more subjects suspected of having the colorectal or gastroenterological cancer, mixing the stool sample with a sodium chloride solution, RNase free water, or both to form a suspension, wherein the stool sample to sodium chloride solution ratio is 1:10, centrifuging the suspension, separating a supernatant from the centrifuged suspension, measuring a total RNA/miRNA concentration in the supernatant using a spectrophotometer, transcribing a cDNA from the total RNA using one or more specific miRNA primers, amplifying the transcribed cDNA using a polymerase chain reaction assay to obtain one or more amplified miRNAs, and comparing the levels of the one or more miRNAs from the stool samples of the one or more subjects suspected of having the colorectal or gastroenterological cancer with that of one or more healthy subjects; wherein an elevated level of the one or more miRNAs indicates the presence of the colorectal or gastroenterological cancer.

In another embodiment the present invention provides a method of processing a biological sample for amplification of once more target MicroRNAs (miRNAs) in the sample without a prior extraction of the one or more miRNAs comprising the steps of: (i) mixing the biological sample with a salt solution, RNase free water, or both to form a suspension, (ii) centrifuging the suspension, (iii) separating a supernatant from the centrifuged suspension, and (iv) storing the supernatant at $-80°$ C. or processing the supernatant immediately to amplify the one or more miRNAs by a polymerase chain reaction. The method described hereinabove comprises an additional optional step of filtering the supernatant prior to storage or processing. In one aspect the biological sample is a stool sample and the salt solution is a sodium chloride solution. In another aspect ratio of the stool sample to sodium chloride solution is 1:10. In yet another aspect the ratio of the stool sample to sodium chloride solution is 1:1, 1:2, 1:5, 1:10, 1:20, 1:25, 1:50, and 1:100.

BRIEF DESCRIPTION OF THE DRAWINGS

For a more complete understanding of the features and advantages of the present invention, reference is now made to the detailed description of the invention along with the accompanying figures and in which:

FIGS. 8A-8E show the microRNA expression in stool from healthy subjects: (8A) microRNA array was performed on the stool and normal colonic mucosa tissue. Heatmap represents similarities and differences in expression profiles, (8B) microRNA expression among independent extractions from the same fecal samples show strong reproducibility and correlation, raw (8C) and normalized (8D) inter-individual variations of microRNA expression measured in stool samples of 8 healthy subjects (normalization was performed using the standard delta Ct method), (8E) stool samples collected at different time points show significant correlation between miRNA expression patterns.

DETAILED DESCRIPTION OF THE INVENTION

Figure 1:
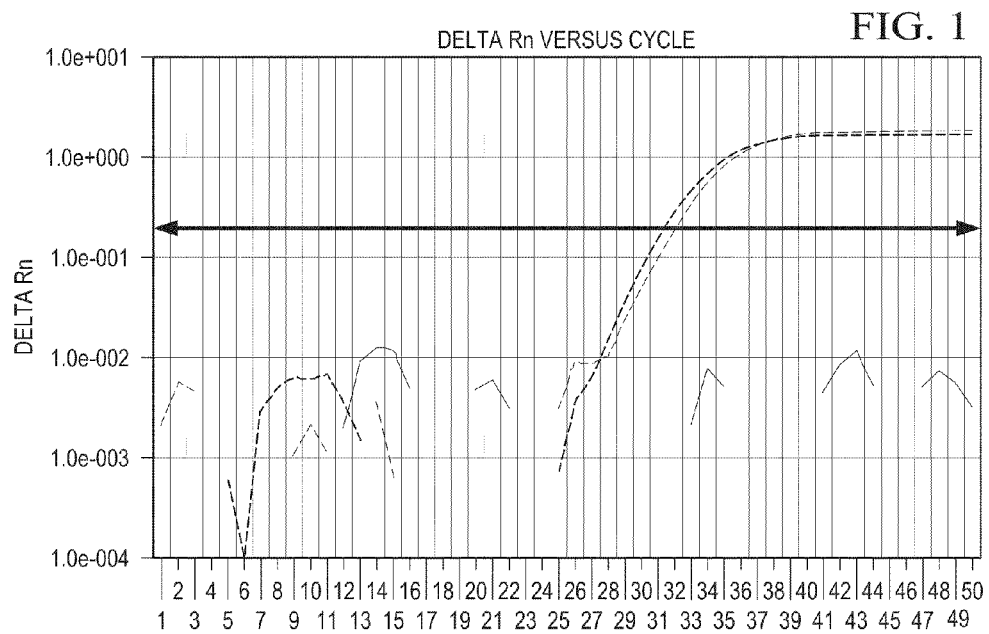
FIG. 1 shows the real time polymerase chain reaction (PCR) data demonstrating robust amplification of mir-29a in stool specimens using a phenol-chloroform based method (Qiagen's miRNAeasy kit) with modifications: Real time PCR was performed as described in the Methods section. The PCR amplification profiles represent detection of miRNA (mir-29a) in stool in duplicates. The blue line on the bottom represents the negative control (water only)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "colorectal cancer" includes the well-accepted medical definition that defines colorectal cancer as a medical condition characterized by cancer of cells of the intestinal tract below the small intestine (i.e., the large intestine (colon), including the cecum, ascending colon, transverse colon, descending colon, sigmoid colon, and rectum). Additionally, as used herein, the term "colorectal cancer" also further includes medical conditions which are characterized by cancer of cells of the duodenum and small intestine (jejunum and ileum).

As used herein, the term "microRNA" ("miRNA") refers to all RNA (or RNA analog) comprising the product of an endogenous, non-coding gene whose precursor RNA transcripts can form small stem-loops from which mature "miRNAs" are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003b; Lagos-Quintana et al., 2003; Lim et al., 2003a; Lim et al., 2003b). "miRNAs" are encoded in genes distinct from the mRNAs whose expression they control.

The term "biomarker" as used herein in various embodiments refers to a specific biochemical in the body that has a particular molecular feature to make it useful for diagnosing and measuring the progress of disease or the effects of treatment. For example, common metabolites or biomarkers found in a person's breath, and the respective diagnostic condition of the person providing such metabolite include, but are not limited to, acetaldehyde (source: ethanol, X-threonine; diagnosis: intoxication), acetone (source: acetoacetate; diagnosis: diet/diabetes), ammonia (source: deamination of amino acids; diagnosis: uremia and liver disease), CO (carbon monoxide) (source: $CH_2Cl_2$, elevated % COHb; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), H2S (source: metabolism; diagnosis: periodontal disease/ovulation), MeS (source: metabolism; diagnosis: cirrhosis), and Me2S (source: infection; diagnosis trench mouth).

As used herein the term "genetic marker" refers to a region of a nucleotide sequence (e.g., in a chromosome) that is subject to variability (i.e., the region can be polymorphic for a variety of alleles). For example, a single nucleotide polymorphism (SNP) in a nucleotide sequence is a genetic marker that is polymorphic for two alleles. Other examples of genetic markers of this invention can include but are not limited to microsatellites, restriction fragment length polymorphisms (RFLPs), repeats (i.e., duplications), insertions, deletions, etc.

The term "polymerase chain reaction" (PCR) as used herein refers to the method of K. B. Mullis, U.S. Pat. Nos. 4,683,195, 4,683,202, and 4,965,188, hereby incorporated by reference, which describes a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter PCR).

The term "stool" as used herein is a clinical term that refers to feces excreted by humans. The term "tissue sample" (the term "tissue" is used interchangeably with the term "tissue sample") should be understood to include any material composed of one or more cells, either individual or in complex with any matrix or in association with any chemical. The definition shall include any biological or organic material and any cellular subportion, product or by-product thereof. The definition of "tissue sample" should be understood to include without limitation sperm, eggs, embryos and blood components. Also included within the definition of "tissue" for purposes of this invention are certain defined acellular structures such as dermal layers of skin that have a cellular origin but are no longer characterized as cellular.

The present invention detects miRNA-based biomarkers that can be detected in human stool specimens. The inventors have utilized two different approaches for miRNA-based biomarker detection using: a commercially available phenol-chloroform based method using kit for miRNA extraction from tissue or blood; with some modifications, the inventors have demonstrated that miRNA can be extracted from stool specimens. The inventors have optimized the conditions, and were able to amplify miRNA directly from stool specimens without any prior miRNA extraction (direct miRNA analysis—DMA). The method for miRNA detection in a stool sample as described in the present invention is simple, rapid, inexpensive, and is a very promising and inexpensive tool for commercial biomarker assay development for multiple diseases.

The present invention finds applications in: (i) cancer screening, (ii) differential diagnosis between various CRC types, (iii) diagnosis of other gastrointestinal cancers (gastric, pancreatic, esophageal, liver cancers etc.), (iv) planning of cancer treatment, (v) evaluation of cancer prognosis, and (vi) surveillance (secondary screening) in cancer patients after initial therapy, (vii) as well as other acquired or hereditary disorders.

Gastrointestinal cancers account for approximately 25% of all cancer deaths in the Western world, and among these, colorectal cancer (CRC) is one of the most frequent cancers. Colorectal cancer (CRC) is the second leading cause of cancer deaths in adults in the United States (1). In 2007, there were ~154,000 new eases of CRC in the United States, with ~52,000 related deaths (1). The high mortality of this disease is due to late-stage diagnosis, where the CRCs have developed extended local growth and distant metastasis. Thus, early detection of these neoplasms is critical because of the direct impact on prognosis. Therefore, new robust and reliable diagnostic approaches that can improve the existing screening strategies are urgently needed. Even though the need for such diagnostic tools has been long recognized, there has only been a modest success in the development of effective interventional approaches (2, 5). Clinical and basic research studies have contributed enormously to our understanding of the complex carcinogenetic processes in CRC. This is a multi-step disease that involves the stepwise accumulation of genetic and epigenetic alterations that activate and promote the progression of neoplasms from premalignant lesions (adenomas) to cancers, and this usually takes several years to develop. Diagnosis in the early stage makes it possible to tailor effective endoscopic or surgical treatments. Moreover, the development of cancer may be prevented through polyp removal. Although endoscopic screening remains the gold standard for early detection, the overall participation in CRC screening programs is still fairly low and is also associated with high costs and patient discomfort. For these reasons, a noninvasive procedure using biomarkers for early detection of colorectal neoplasia constitutes a priority in the prevention of this disease (2). In addition, utilization of such preventive strategies using robust biomarkers would allow stratification of patients into appropriate screening or surveillance programs.

Endoscopic procedures such as colonoscopies are very accurate and permit the removal of adenomas, which reduce cancer incidence. However, this procedure has several practical limitations, as it requires bowel preparation, sedation, is associated with a risk of serious medical complications, and is expensive. Clinical guidelines recommend screening colonoscopy beginning at age 50, but in >80% of individuals the procedure could be potentially spared since no important lesions are found (7). Therefore, an optimal screening test may reduce the necessity for an invasive procedure, reduce the cost, have good screening compliance and could more accurately select individuals at risk who require a neoplastic lesion be removed colonoscopically. Whereas CT colonography fulfills some of these criteria, there is concern about the high radiation exposure that can itself be theoretically associated with cancer risk (8).

Most noninvasive molecular tests are based on the analysis of feces and/or blood. Guaiac-based fecal occult blood testing (FOBT) is the most commonly used test which detects occult blood in stool. FOBT screening has been associated with reduction in CRC related mortality by 15%-33% (9). However, this test has several limitations, including low specificity and sensitivity in the detection of CRC's (33-50%) and colon adenoma (11%) (10). Another promising approach for the identification of colorectal and other rumors is to assay stool or bodily fluids for molecular biomarkers that represent the spectrum of genetic and/or epigenetic alterations associated with cancer. Based upon this paradigm, fecal DNA based testing has been an area of active investigation since early 1990s (5). There is constant sloughing and shedding of tumor cells into stool from the neoplastic tissues, which provide the substrate for the discovery of cancer-related genetic 'signatures'. Genetic markers for CRC have been based on the identification of alterations in a subset of genes including APC, p53 and K-Ras (5). Even though some versions of these tests are being offered commercially, they are cumbersome to perform, and provide a modest diagnostic sensitivity of ~50-80% for invasive cancers, and 18-40% for advanced benign neoplasms (5, 10, 11). More recently, there has been growing interest in exploiting fecal based testing for another DNA-based target, i.e., aberrant hypermethylation of CpG islands. In a cohort of patients with various GI lesions, our group has recently shown that aberrant methylation of two genes significantly improved sensitivity and specificity for the detection of gastrointestinal neoplasia (12).

The main goal for developing a non-invasive biomarker in CRC prevention is their ability to detect the signs of neoplastic disease in the earliest stage, preferably when it is still an adenoma. Noninvasive biomarkers have a long history starting with the development of carcinogenic embryonic antigen (CEA) in the serum. Serum CEA is not used for CRC screening due to its low sensitivity and specificity. Furthermore, most serum-based tests have failed due to their lack of sensitivity or specificity. However, due to the ease of application of serological approaches, there is a continuous effort to develop blood-based cancer biomarkers.

Nearly all of the currently available non-invasive screening tests rely on the use of stool samples. Stool-based detection of heme or globin through chemical or immunological reactions are the most extensively evaluated approaches, and these are referred to as fecal occult blood tests (FOBTs) or fecal immunochemical tests (FITs). The utility of FOBTs has been repeatedly evaluated in clinical studies that have shown reduced cancer-associated mortality by 15-33% as a result of the detection early stage cancers, and perhaps the removal of adenomaious polyps. With a specificity of 88-98%, the main limitation of FOBT is its poor sensitivity (15-30%), especially when used through a single digital exam (3, 4). This limitation has been partially resolved with the use of the newer generation FOBTs and FITs, repetitive testing and rehydration of the stool specimens that improve the sensitivity to perhaps 60%—but compromise specificity. Nevertheless, although the majority of individuals without disease will have a negative FOBT test, the rate of false positive results is still very high due to other sources of gastrointestinal bleeding and biochemical false positives, and the consequence is very low positive predictive values.

Biomarker detection in fecal specimens has been an area of active investigation since the early 1990s (5). This approach is based upon the fact that there is a constant sloughing and shedding of tumor cells from the neoplastic tissues, which may provide the substrate for the discovery of 'signatures' for the genomic abnormalities present in gastrointestinal neoplasia. Genetic markers for CRC have been based upon the identification of alterations in a subset of genes including adenomatous polypasis coli (APC), p53 and K-Ras (5). Even though some of these tests are being offered commercially, these assays require a large volume of fecal sample, involve complex processing of fecal materials to obtain high quality human genomic DNA, and provide a modest diagnostic sensitivity of 52% for invasive cancers, and 18% for the detection of advanced neoplasms. These tests have been optimized by improving the recovery of DNA from the stools, but are limited by the fact that many CRCs simply do not have any of these genetic abnormalities, and will never be detected using these technologies.

MicroRNAs (miRNAs) are small non-coding transcripts that have been recently identified as a new class of cellular molecules with high diagnostic, prognostic and therapeutic implications (13, 14). miRNAs are small transcripts of 19-25 nucleotides that are encoded in the genome of humans, vertebrates and plants. Cross-species comparisons demonstrate that miRNAs are evolutionarily conserved and play an important role in a wide range of physiological and pathological processes. Although the biology of miRNAs is still poorly understood, it is now known that each miRNA may control hundreds of mRNA targets and act as master regulators of gene expression. Recent findings indicate that miRNAs are involved in the pathogenesis of different types of cancers (14, 15). miRNAs can act as oncogenes (oncomiRs) or tumor suppressor genes (tsmiRs) and that they are involved in the early stages of carcinogenesis. Moreover, the pattern of miRNA expression can be used to classify diverse types and also subtypes of cancers and miRNA expression profiles can have prognostic and therapeutic implications (6). All these features make miRNAs a very exciting and promising tool for early tumor detection. Expression patterns of miRNAs are systematically altered in colon adenocarcinomas. High miR-21 expression is associated with poor survival and a poor therapeutic outcome (6). The use of miRNA as a potential biomarker in CRC prevention has been recently evaluated in plasma in order to discriminate patients with and without CRC, showing that miR-92 is significantly elevated in the plasma of CRC patients compared to healthy individuals. However, there are still no data on the usefulness of miRNA in the blood of patients with adenomas. Although a blood test is potentially a promising approach for CRC detection, it is more likely that the earliest changes in miRNA expression would be detectable in feces prior to their appearance in blood. For this, miRNA analysis in stool samples, which has not been performed until now, would be a novel and promising non-invasive tool for detecting colon adenomas, CRCs and other gastrointestinal neoplasms. Moreover, miRNAs have also been promoted for its potential as a target for cancer therapy. It is anticipated that further research will elucidate the benefits of using miRNAs as clinical agents in the battle against cancer and other chronic diseases. One of the most exciting biological features of miRNA compared to mRNA is that they are present in different tissues in a very stable form and due to their small size are remarkably protected from endogenous degradation (16-18). Although miRNAs have been detected in tumor tissues, serum, plasma and urine suggesting them as exciting and promising tools for early tumor detection, the detection of miRNAs in stool has not been reported (19).

The present invention demonstrates that microRNAs can be easily detected in stool specimens from both healthy subjects and patients with colorectal disease. Pilot analyses of the stool specimens from patients with CRC and colonic adenoma suggests a potential role of fecal microRNAs as novel biomarkers in early detection of colorectal neoplasia.

miRNAs interact with messenger RNA and participate in gene expression regulation during cell development and differentiation by inducing either mRNA degradation or translational inhibition. Cross-species comparisons demonstrate that miRNAs are evolutionarily conserved and play important roles in a wide array of normal biological processes.

Stool specimens from healthy subjects: The present inventors collected fresh stool samples from 8 healthy individuals (4 male and 4 female, mean age 28.9 years). Fresh stool specimens collected were immediately frozen at −80° C. until RNA isolation was performed. The stool samples collected in FOBT kits or any other source were kept at −20° C. after collection before reaching the laboratory.

Clinical Samples: A total of 29 stool specimens collected in fecal occult blood test kits were obtained from 10 individuals with normal colonoscopy, 9 patients with advanced and non-advanced colonic adenomas, and 10 patients with CRC at the Okayama University Hospital, Okayama, Japan. Clinical and demographical data of the patients are presented in Table 1.

miRNA extraction from stool specimens using modified phenol chloroform based methods: Extraction of miRNA from stool specimens was performed with a phenol-chloroform based kit (Qiagen's miRNA easy Mini kit) with some modifications, which is designed for miRNA extraction from tissue and blood specimens. 20-100 mg of frozen stool was mixed with QIAzol Lysis Reagent in the proportion 1:7-10 (stool:lysis reagent, a solution containing phenol and guanidine thiocyanate) and vortexed thoroughly for 60 sec. The stool specimen was placed in a QIAshredder homogenizing column and centrifuged at a maximum speed of 14,000 rpm for 2 min. at room temperature (RT). Thereafter, the QIAshredder column was discarded and the tube lid was closed and placed at the bench top for 5 min. at RT. Subsequently, chloroform was added to this mix in the proportion 5:1 (lysed stool:chloroform), and the contents were pipetted up and down several times to allow thorough mixing, followed by brief vortexing for 3-5 sec. The tube was then left on the bench top for an additional 2-3 min. at RT. This was followed by centrifugation for 15 min. at 14,000 rpm at 4° C. The upper (aqueous) phase was transferred to a new collection tube and mixed with 1.5 volumes of 100% ethanol and the contents were mixed thoroughly by pipetting up and down several times. Up to 700 µl of the content of the tube was transferred to an RNAeasy Mini spin column supported in a 2 ml collection tube. The tube was centrifuged at 10,000 rpm for 30 s at RT. The flow through was discarded and if necessary, the previous step was repeated with the rest of the mixture one more time. 700 µl of the RWT buffer was added to the RNA easy Mini spin column, followed by centrifugation for 30 s at 10,000 rpm at RT. The flow through was discarded and 500 µl of Buffer RPE was added to the RNAeasy Mini spin column. Centrifugation was repeated at 10,000 rpm for 30 s at RT. The flow through was discarded and another 500 µl of Buffer RPE was added to the RNA easy Mini spin column. Centrifugation was repeated at 10,000 rpm for 2 min. at RT and the RNA easy Mini spin column was placed into a fresh 2 ml collection tube and centrifuged at full speed at RT for 1 min. The RNA easy Mini spin column was transferred to a new 1.5 ml collection tube. Approximately 30-50 µl of RNase-free water was added directly onto the column membrane. The contents were allowed to sit on the bench top for 5 min. and then centrifuged at 10,000 rpm for 1 min. at RT to elute the total miRNA/RNA in the RNase-free water. Following the extraction, the samples were placed on ice for further analysis or stored at −80° C. The phenol-chloroform method is based on the principle of homogenization or lysis with phenol and guanidine isothiocyanate, followed by separation with chloroform the RNA from aqueous phase. This is followed by RNA precipitation with isopropyl alcohol, washing with 75-100% ethanol, air drying, and redissolving the pelleted RNA with RNase free water.

TABLE 1

Clinico-pathological characteristics of FOBT samples patients.

| ID | Diagnosis | Gender | Age | TNM stage | Histology | Tumor Location | Proximal/Distal |
|---|---|---|---|---|---|---|---|
| N1 | N | M | 70 | — | — | — | — |
| N2 | N | F | 79 | — | — | — | — |
| N3 | N | M | 46 | — | — | — | — |
| N4 | N | M | 76 | — | — | — | — |
| N5 | N | M | 79 | — | — | — | — |
| N6 | N | M | 82 | — | — | — | — |
| N7 | N | M | 77 | — | — | — | — |
| N8 | N | F | 79 | — | — | — | — |
| N9 | N | M | 67 | — | — | — | — |
| N10 | N | F | 72 | — | — | — | — |
| A1 | NAA | M | 55 | — | LGD | As&S | D |
| A2 | NAA | F | 76 | — | LGD | As | P |
| A3 | NAA | M | 52 | — | LGD | S | D |
| A4 | NAA | F | 74 | — | LGD | S | D |
| A5 | AA | F | 41 | — | LGD | D | D |
| A6 | AA | M | 85 | — | LGD | R | D |
| A7 | NAA | M | 55 | — | LGD | As | P |
| A8 | NAA | M | 75 | — | LGD | T | P |
| A9 | AA | M | 69 | — | LGD | As | P |
| C1 | Cancer | F | 75 | 4 | IV | As | P |
| C2 | Cancer | F | 65 | 3 | III | As | P |
| C3 | Cancer | F | 67 | 2 | II | As | P |
| C4 | Cancer | M | 77 | 4 | IV | S | D |
| C5 | Cancer | M | 75 | 4 | IV | S | D |
| C6 | Cancer | F | 53 | 2 | II | R | D |
| C7 | Cancer | F | 57 | 2 | II | As | P |
| C8 | Cancer | M | 47 | 1 | I | D | D |
| C9 | Cancer | F | 51 | 3 | III | As | P |
| C10 | Cancer | F | 65 | 2 | II | D | D |

Abbreviations: M—male, F—female, N—normal, A—adenoma, AA—advanced adenoma, NAA—non-advanced adenoma, C—colorectal cancer, LGD—low grade dysplasia, As—ascending colon, T—transverse colon, D—descending colon, S—sigmoid colon, R—rectum.

Direct miRNA PCR amplification from stool specimens without extraction (Direct MicroRNA Analysis—DMA): In this invention, the inventors have developed a new method which obviates the need for prior miRNA extraction called as Direct miRNA Analysis (DMA). The stool specimens were suspended in RNase free water or 0.89% NaCl by taking 1 volume of stool specimen and mixing it with 10 volumes of NaCl solution (1:10 dilution). Diluted stool specimens were thereafter centrifuged at 4,000×0 g for 5-10 min. at 4° C. Optionally, the supernatant was further filtered with a 0.2 µm filter and either stored at −80° C. until used, or immediately processed for direct amplification of a target miR.

Measurement of RNA: The concentration of total RNA/miRNA was optionally measured with a spectrophotometer (Beckman Coulter DU®530 Life Science UV/Vis Spectrophotometer).

MicroRNA microarray expression profiling and data analysis: In order to explore the miRNA expression signature between fecal specimens and the normal colonic mucosal tissues, the inventors analyzed the miRNA expression profiles in 5 normal colonic mucosa tissues and one stool sample from a healthy individual. RNA was amplified and subsequently hybridized to the SAM-Bead microarray according to the manufacturer's instructions (Illumina, Inc., San Diego, Calif.). Microarray data processing and analysis were performed using Illumina BeadStudio software. Data were processed and normalized using Lumi Bioconductor software package (28). The inventors employed a conservative probe-filtering step which excluded probes that did not reach a detection p-value <0.05. This analysis resulted in the reliable detection of 912 probes from a total of 1145 probes on the microarray chip. GeneSpring OX 7.3 software (Agilent Technologies) was used for data analysis and image generation.

Reverse transcription (RT): Reverse transcription was performed using the stem-loop primer based method. In particular, three TaqMan MicroRNA assays analyzed in this application were predesigned assays purchased from Applied Biosystems, CA. The assays included mir29a (hsa-mir-29a, ASI assay ID 002112), mir370 (hsa-mir-370, ABI assay ID 002275) and RNU6b (ABI assay ID 001093).

Quantification of miRNA: Quantification of miRNA was performed using either TaqMan miRNA Assays (Applied Biosystems) or SYBRgreen method, with some modifications (18, 20). Briefly, ~20 ng of RNA was reverse transcribed and real-time quantification was performed using Applied Biosystems 7300 Sequence detection system. All reactions were run in triplicates. Primer sequences for the RT-PCR assays are listed in Table 2. Selection of miRNAs (miR-21, -17, -25, -29b, -106a, -143, -654-3p, -622, -1238, and -938) was performed based on the following criteria: 1) previously published with potential implication in cancer development; 2) differential expression between stool and normal colonic mucosa based on miRNA microarray data; and 3) differential expression between colon cancer and normal mucosa (unpublished data Balaguer et al.). Differences between groups are presented as ΔCt, indicating the difference between the Ct value of the miRNA of interest and the Ct value of the normalizer miRNA. Selection of the targets for normalization was carried out based on the previous publications and coherence of endogenous Ct signals (21, 22).

Real time PCR reaction: In the PCR step, PCR products are amplified from cDNA samples using the TaqMan MicroRNA Assay (Applied Biosystems, California, USA) together with the TaqMan Universal PCR Master Mix (Applied Biosystems, California, USA). Accordingly, the reverse transcription products were used in a total reaction volume of 20 uL for relative quantification by Real-Time PCR using an Applied Biosystems 7000 Sequence Detection System with the following components; 1 uL of TaqMan MicroRNA Assay (20X), 6 uL of product from the RT reaction, 10 uL of Taq-Man 2X Universal PCR Master Mix No AmpErase UNG (Applied Biosystems, California, USA) and 3 uL of Nuclease-free water. The thermal cycling program used for amplification was as follows: 95° C. for 10 min. followed by 40 cycles of 95° C. for 15 sec. and 60° C. for 60 sec.

TABLE 2

Primers for qRT-PCR.

| Name | TaqMan Assay ID | Syber-Green | miRBase Accession | References |
|---|---|---|---|---|
| RNU6b | 001093 | | | |
| miR-106a | 002169 | | MIMAT0000103 | |
| miR-1238 | 002927 | | MIMAT0005593 | |

TABLE 2-continued

Primers for qRT-PCR.

| Name | TaqMan Assay ID | Syber-Green | miRBase Accession | References |
|---|---|---|---|---|
| miR-143 | 002249 | | MIMAT0000435 | |
| miR-16 | 000391 | | MIMAT0000069 | |
| miR-17 | | + | MIMAT0000070 | Chen et al. (18) |
| miR-21 | | + | MIMAT0000076 | Chen et al. (18) |
| miR-25 | | + | MIMAT0000081 | Chen et al. (18) |
| miR-26b | | + | MIMAT0000083 | Chen et al. (18) |
| miR-29b | 000413 | | MIMAT0000100 | |
| miR-622 | 001553 | | MIMAT0003291 | |
| miR-654-3p | 002239 | | MIMAT0004814 | |
| miR-938 | 002181 | | MIMAT0004981 | |

Statistical analysis: Data analyses were performed with Graph Pad Prism 4.0 software (San Diego, Calif., USA). The differences between two groups were analyzed using Student's t-tests and between more than two groups were analyzed using ANOVA or Kruskall-Wallis with appropriate post hoc test. Correlation analyses were performed using Spearman's test. Two sided p-values of <0.05 were regarded significant.

Figure 7A:
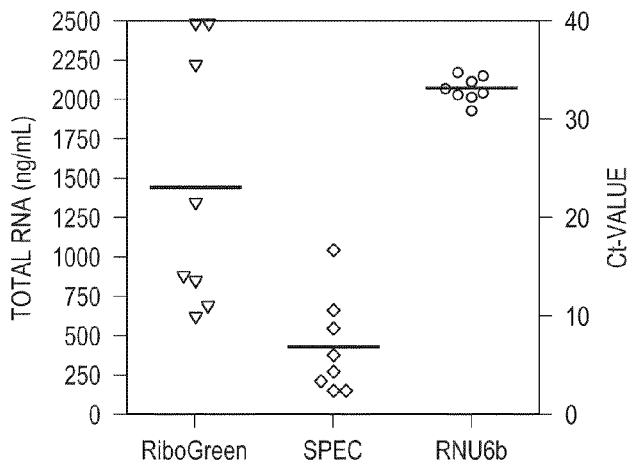
FIGS. 7A-7F show the total RNA and microRNA detection in stool of healthy subjects; (7A) RiboGreen was used to measure total RNA concentration in stool samples. High variation of total RNA concentration measured by RiboGreen shows no correlation to RNU6b, both total RNA concentration (7B) and RNU6b (7C) expression levels show significant correlation among independent extractions, (7D) comparison of Ct values detected by qRT-PCR for various miRNAs shows significant correlation between direct miRNA analyses (DMA) method and miRNA from Qiagen kit extracted samples, (7E) 3 housekeeping RNA/microRNAs were evaluated for possible use as internal control. RNU6b shows high degree of variations and shows no significant correlation to mir-16 and -26b, (7F) miR-16 and -26b reveal constant profiles among different individuals and also demonstrates a significant correlation between expression levels.
Figure 7B:
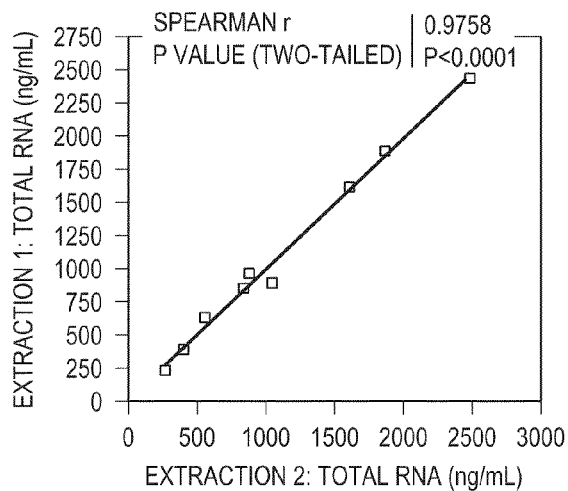
Figure 7C:
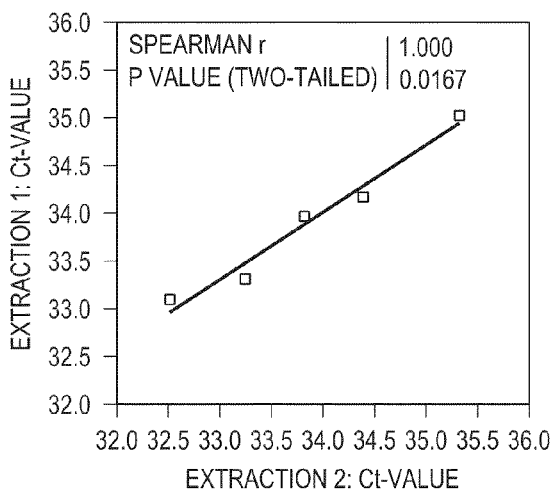

Fecal RNA: extraction and reproducibility: Given the fact that miRNAs have previously been shown to be present in other bodily fluids, the inventors evaluated the presence of microRNA in stool. Following optimization and modification of existing commercial kits recommended for total RNA extraction, the inventors were able to isolate an adequate amount of total fecal RNA from 8 healthy individuals. The RNA concentrations in stool ranged from 622 to 2475 ng/μl, which did not correlate to RNU6b expression (FIG. 7A). To evaluate the integrity of small RNAs, the present inventors performed qRT-PCR analysis which robustly amplified RNU6b, a small nuclear ubiquitary RNA ~50 bp, which is commonly used as endogenous control in miRNAs studies (FIG. 7A). To assess the reproducibility of the miRNA extraction methodology, the inventors repeated this procedure in a subset of samples. As shown in FIGS. 7B and 7C, the results were highly reproducible, both in terms of total RNA concentrations ($r=0.97$, $p<0.0001$) and for RNU6b expression levels ($r=1$, $p=0.016$).

Figure 7D:
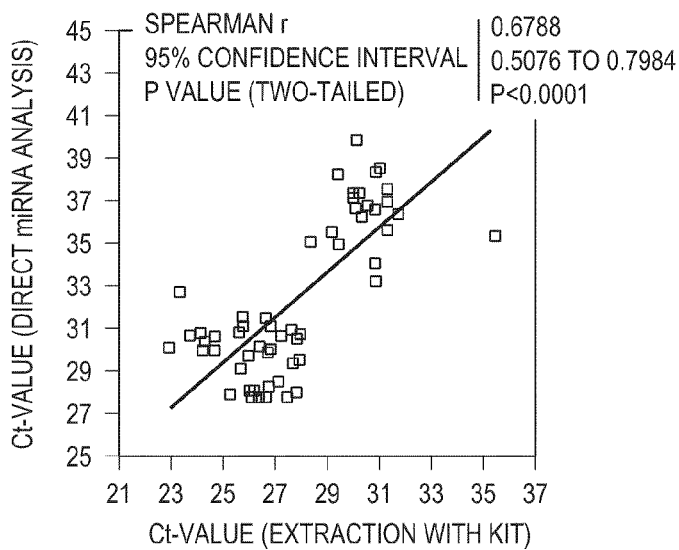

Direct microRNA analysis (DMA): miRNAs have been shown to be present in blood both as intracellular entities and extracellular as content of exosomes (17, 18). In order to evaluate the feasibility of detecting extracellular miRNAs in stool, the present inventors developed a new method called DMA, which obviates the need for RNA extraction prior to expression analysis. The inventors compared the expression levels of different miRNAs in healthy subjects using both RNA extraction with QIAGEN kit and DMA (FIG. 7D). Although the miRNA expression levels were lower using DMA, the inventors found significant correlation between Ct values between both methods.

Figure 7E:
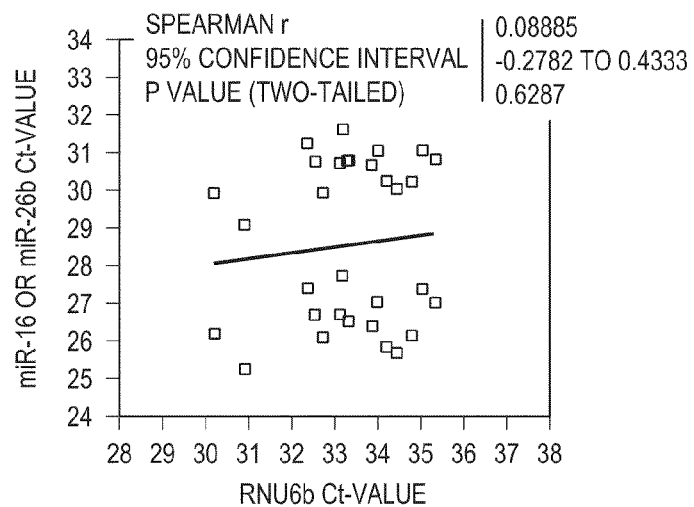
Figure 7F:
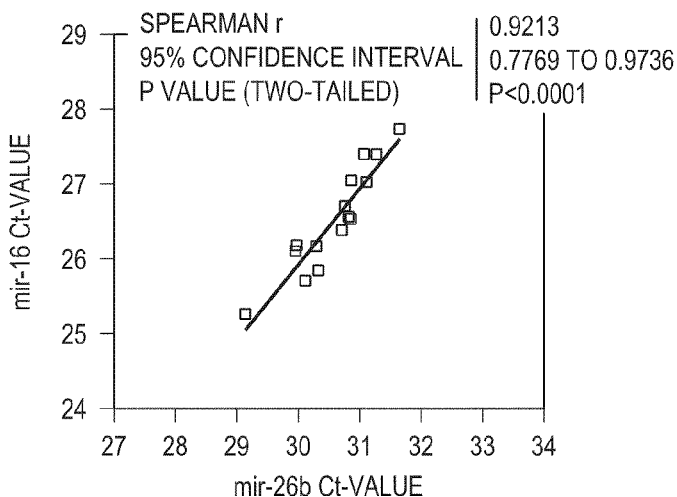

Fecal microRNA: reliable normalization to housekeeping microRNAs: Several reports (17, 18) have clearly shown that, in contrast to messenger RNAs, miRNAs are remarkably stable at high temperatures and are barely affected by ribonucleases induced degradation. RNU6b, as previously mentioned, is commonly used as endogenous control in miRNAs studies; however, unlike miRNAs, its stability and significance as an endogenous normalization control has recently been questioned (14, 18). In this study, the inventors found that RNU6b did not correlate with either of previously described normalizers such as miR-16 and -26b (FIG. 7E). However, both miR-16 and miR-26b expression pattern showed a highest coherence among different samples as well as significant correlation (r=0.92, p<0.0001) between each other (FIG. 7F). Thus, these two miRNAs were selected as normalizers for further analyses.

Figure 8D:
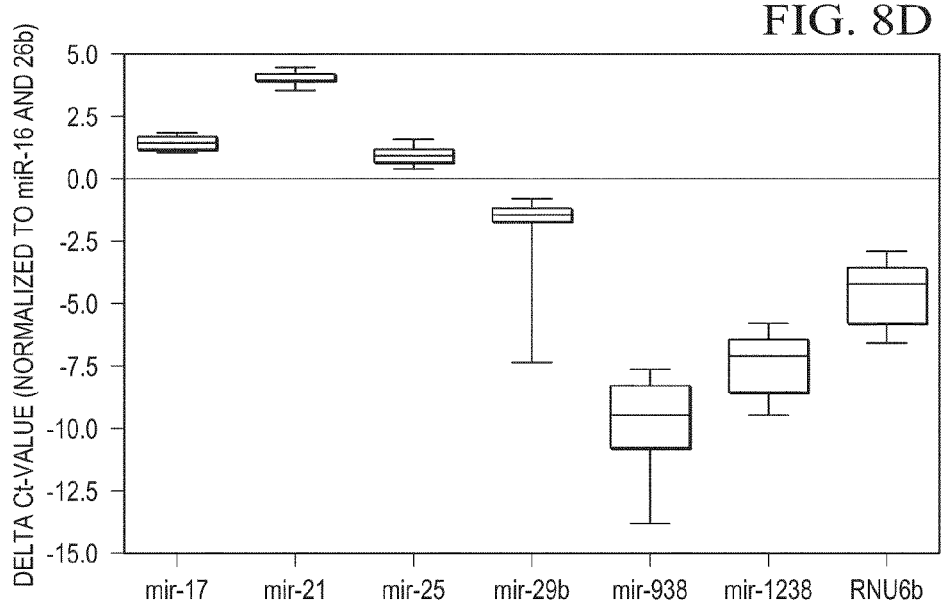

Similar microRNA expression pattern among healthy individuals: The inventors analyzed the expression pattern of a subset of miRNAs among eight healthy individuals. To confirm the reproducibility of the analysis, the studies were repeated in two independent RNA extractions showing a significant correlation (r=0.99, p<0.0001) (FIG. 8B). FIG. 8C shows the raw Ct values of the miRNAs analyzed in this study. The inventors found that miR-21 was the most highly expressed miRNA in the stool, and the expression differences among various miRNAs were more than 10000 fold (ΔCt~14-15) between certain miRNAs (miR-21 vs. miR-938). Analysis of the results after normalization to miR-16 and miR26b revealed that the pattern of miRNA expression was very similar among healthy subjects (FIG. 8D). Following the normalization, an inter-individual variation in miRNA expression among healthy individuals was also observed with a standard deviation between ~ΔCt±0.25 (for miR-17 and miR-21) to ~ΔCt±2.15 (for miR-29b or -938). In particular, the variations in miRNAs expression have correlated to the level of expression and were higher in context of lowly-expressed miRNAs compared to highly expressed miRNAs.

Figure 8E:
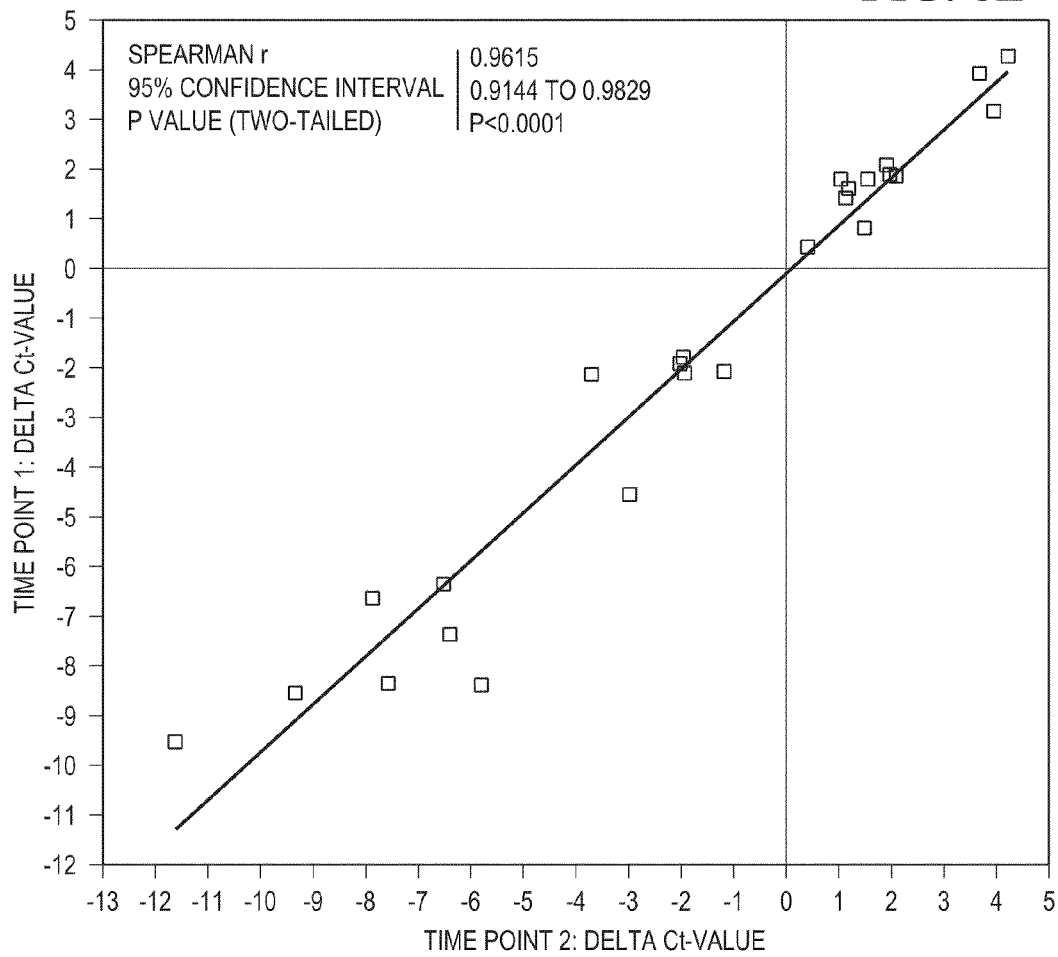

Similarity in microRNA expression pattern at different time points: To explain the biological relevance of stool-based miRNA expression strategy, the inventors studied the differences in the stool miRNA expression patterns in samples collected at different time points (>2 weeks) from the same individuals. This analysis revealed a significant correlation (r=0.96, p<0.0001) of miRNA expression level (FIG. 8E) between two different time points, suggesting that the stool miRNA expression pattern remains constant over time in healthy subjects. Standard deviation of normalized miRNA expression values among healthy individuals varied from ~ΔCt±0.2 (for miR-17 and -21) to ~Ct±0.6 (for miR-938 and -1238).

Comparison of miRNA profiles between stool and normal colonic mucosa: The present inventors further compared the miRNA expression profiles between stool specimen and normal colonic mucosal tissues. As shown in FIG. 8A, the miRNA expression profiles from stool samples and normal colonic mucosa showed significant similarities in the expression profiles of 284 miRNAs which included miR16 and mir26b. These data further provided support and rationale for using these two miRNAs as internal normalizers for the quantification of miRNA expression.

Fecal occult blood test (FOBT) is currently the most frequently used non-invasive test for CRC screening. The feasibility of miRNA detection from FORT kits would facilitate additional possibilities for miRNA-based biomarker identification and validation as a screening tool. Following methodological optimization, the present inventors extracted total RNA including miRNA from FOBT kits from 29 individuals. As expected, the RNA concentration was lower than the fresh stool samples (RNA concentrations varied from 9 to 87 ng/μl). As shown in Table 5, the inventors were able to effectively amplify all examined miRNAs.

Figure 9A:
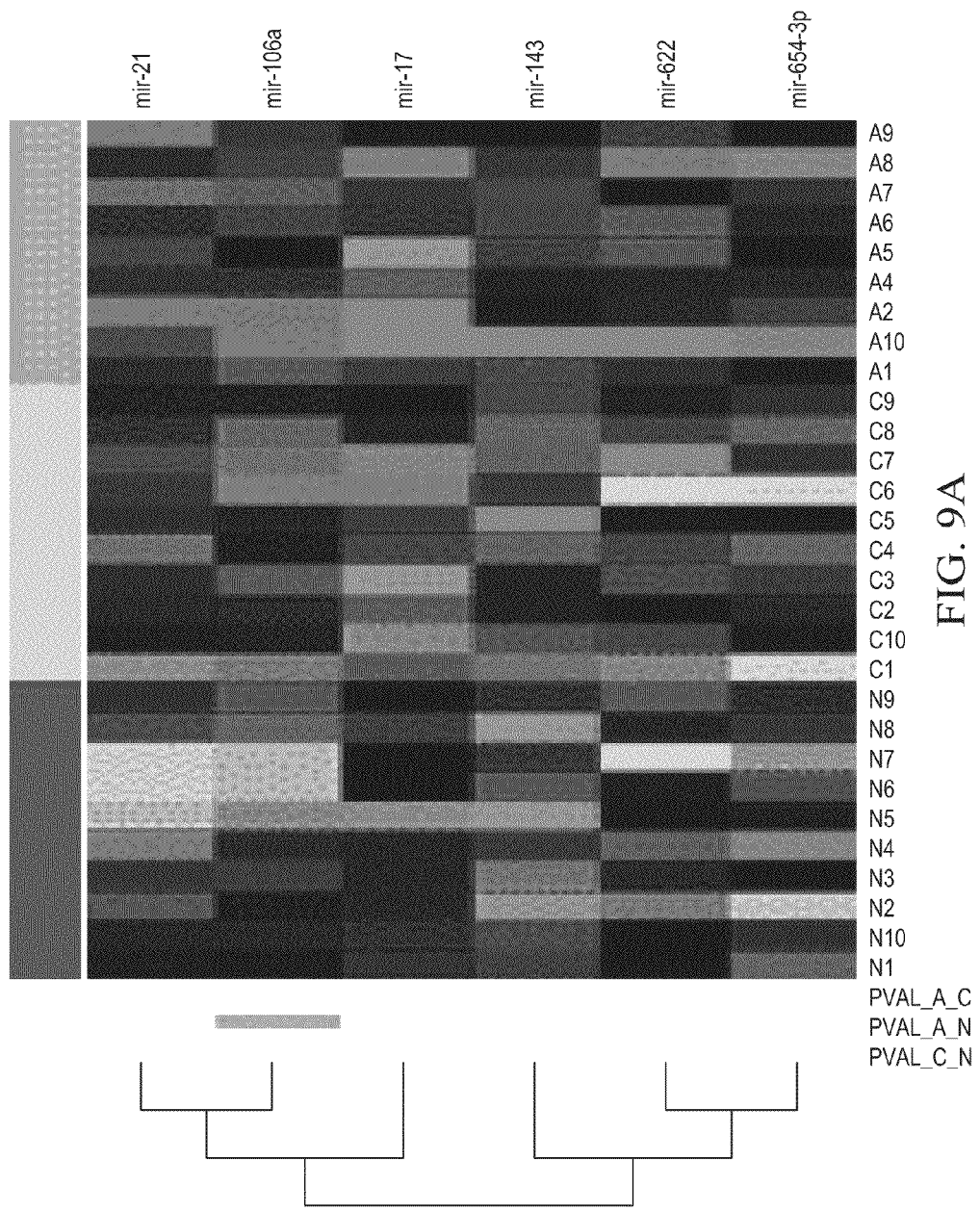
FIGS. 9A-9J show microRNA analysis in normal, adenoma and colorectal cancer patients: (9A) Heatmap of significant genes. miRNA expression between patients with adenomatous polyps and CRC compared to subjects with no endoscopic abnormalities. Plot colors indicate low (green) and high (red) miRNA expression level, (9B-9G) differences in microRNA expression between normal, adenoma and CRC patients. Each figure represents different microRNA, (9H) comparison of microRNA expression between normal and combined adenoma and colorectal cancer patients. qRT-PCR analysis of microRNA expression between subjects with normal colon, and patients with colon neoplasia revealed increased expression of miR-21 and miR-106a in feces from patients with colon neoplasms, (9I and 9J) represent subgroup analysis of mir-21, (9I) and mir-106a, (9J) expression, respectively. The * represents p<0.05. Abbreviations: N—subjects with normal endoscopy, A—adenomatous polyps, C—colorectal cancer, NAA—non advanced adenoma, AA—advanced adenoma.
Figure 9B:
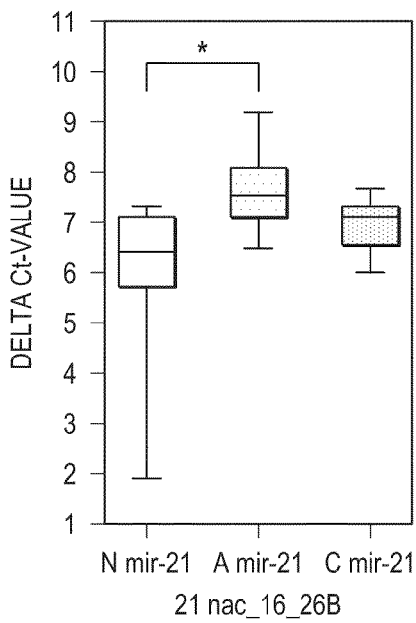
Figure 9C:
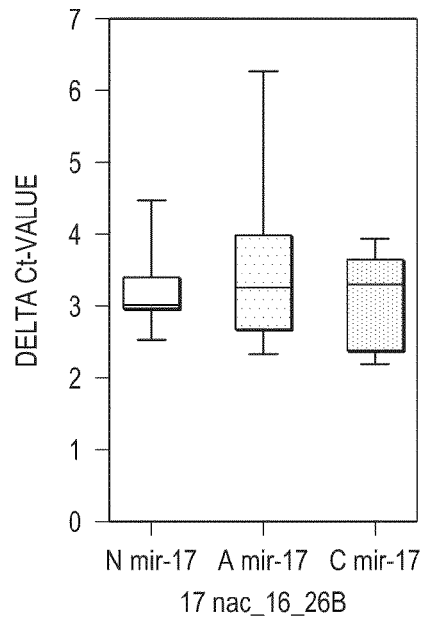
Figure 9D:
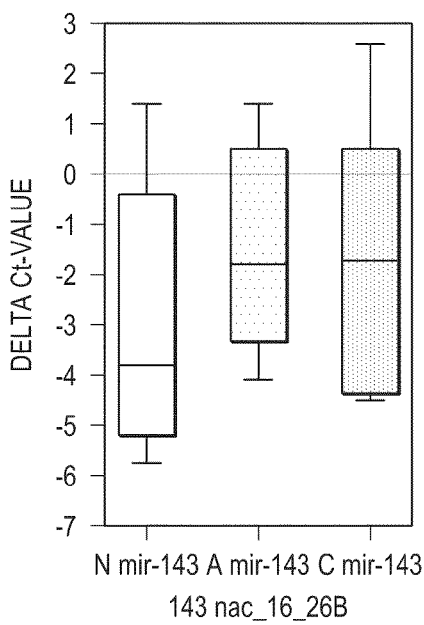
Figure 9E:
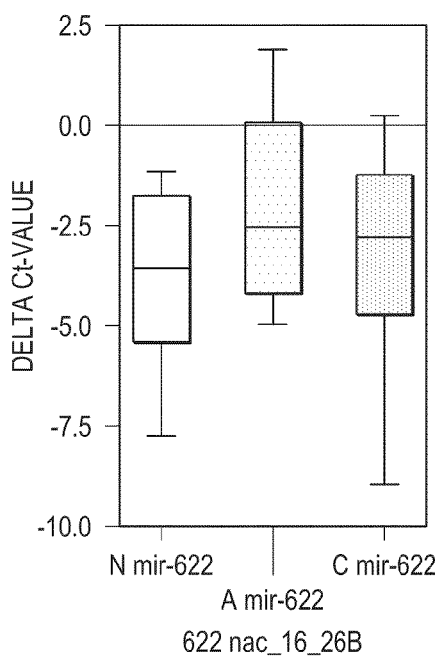
Figure 9F:
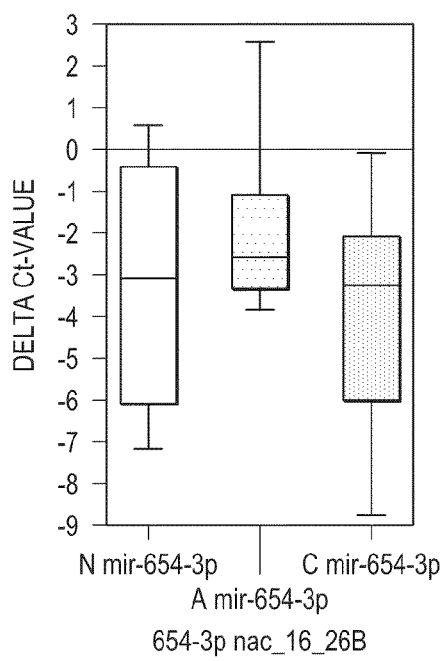
Figure 9G:
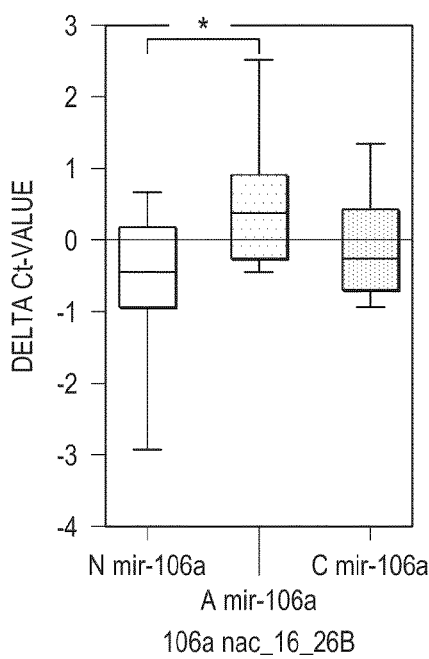
Figure 9H:
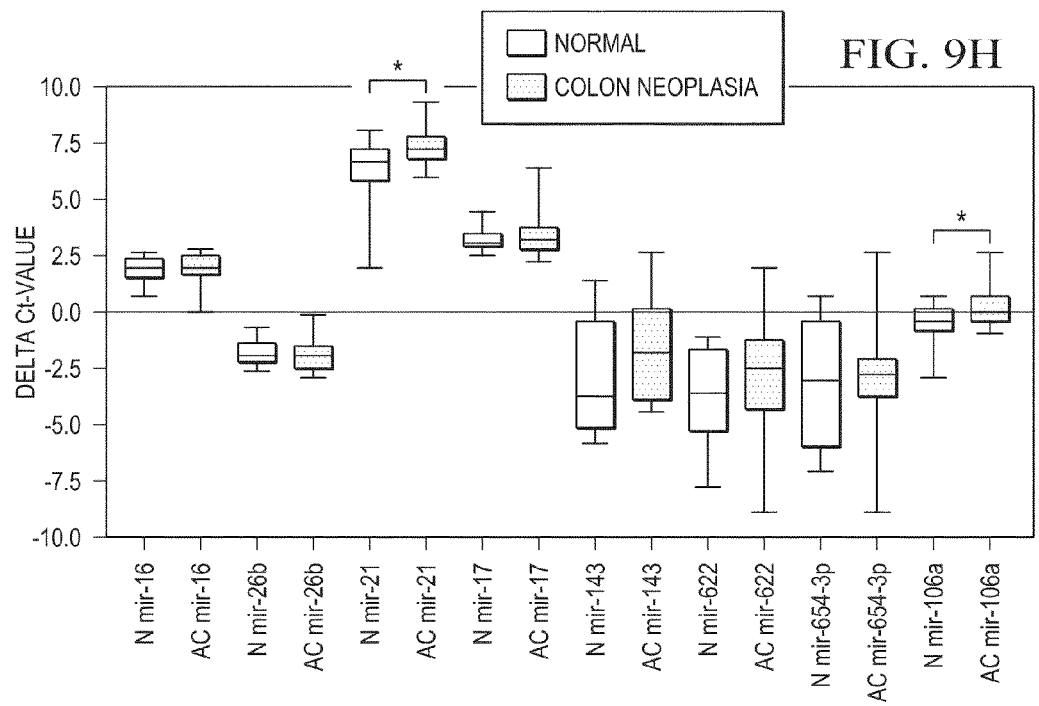
Figure 9I:
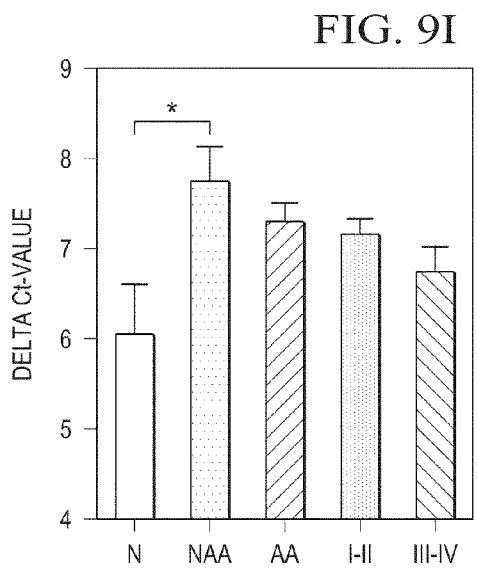
Figure 9J:
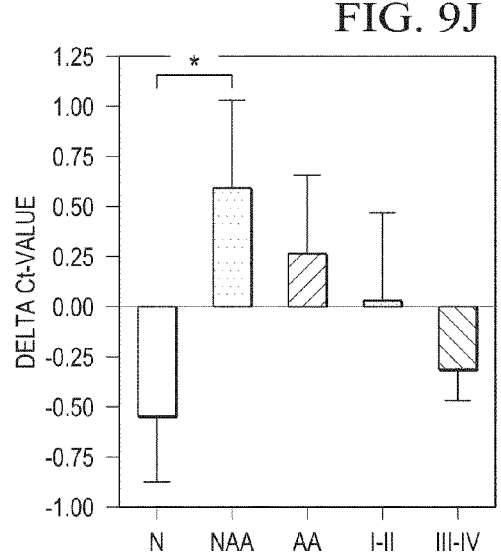

Differential expression of fecal microRNA in patients with colonic neoplasia: Finally, the inventors evaluated the potential use of fecal miRNA expression analysis to discriminate between healthy subjects and patients with colorectal neoplasia (FIGS. 9A and 9H). FIGS. 9B-9G show differences in microRNA expression between normal, adenoma and CRC patients. Each figure represents different microRNA. Interestingly, among 6 tested miRNAs a higher expression of both miR-21 and -106a was found in stool samples from patients with colon neoplasia (adenomas and CRCs) compared to subjects with normal colonoscopy (p<0.05) and no differences were found for miR-17, -143, -622 and -654-3p. Separate analysis of colon adenoma and CRC patients showed that mean ΔCt±SD for miR-21 was 7.6±1.6 and 6.9±0.5 for colon adenoma and CRC patients vs. 6.1±1.6 for subjects with normal colonoscopy (ANOVA p=0.02, Bonferroni's post test normal vs. adenoma p<0.05) and for miR-106a 0.5±1.6 and −0.2±0.05 vs. 0.6±1.6 (ANOVA p=0.05, post test normal vs. adenoma p<0.05), respectively (FIGS. 9B and 9G). Surprisingly, the expression of both miRNAs was found to be higher in stool samples from patients with adenomas compared to CRCs. To further evaluate these associations, the inventors performed the analysis of the miR-21 and -106a expression in subgroups based on the presence of advanced or non-advanced adenomas and TNM tumor stage. Surprisingly, the level of expression of both miRNAs decreased with higher tumor stages (FIGS. 9I and 9J), suggesting the potential dysregulation in miRNA expression pattern in stool with increased shedding of exfoliated colonocytes due to higher tumor stage.

FIG. 1 shows the real time PCR data demonstrating robust amplification of mir-29a in stool specimens using the modified phenol-chloroform based method in particular using Qiagen's miRNA easy kit. Real time PCR was performed as described in the Methods section. The PCR amplification profiles represent detection of mir-29a in stool using modified phenol-chloroform extraction. The results presented in FIG. 1 show robust miRNA extraction and recovery in stool specimens using this method.

Figure 2:
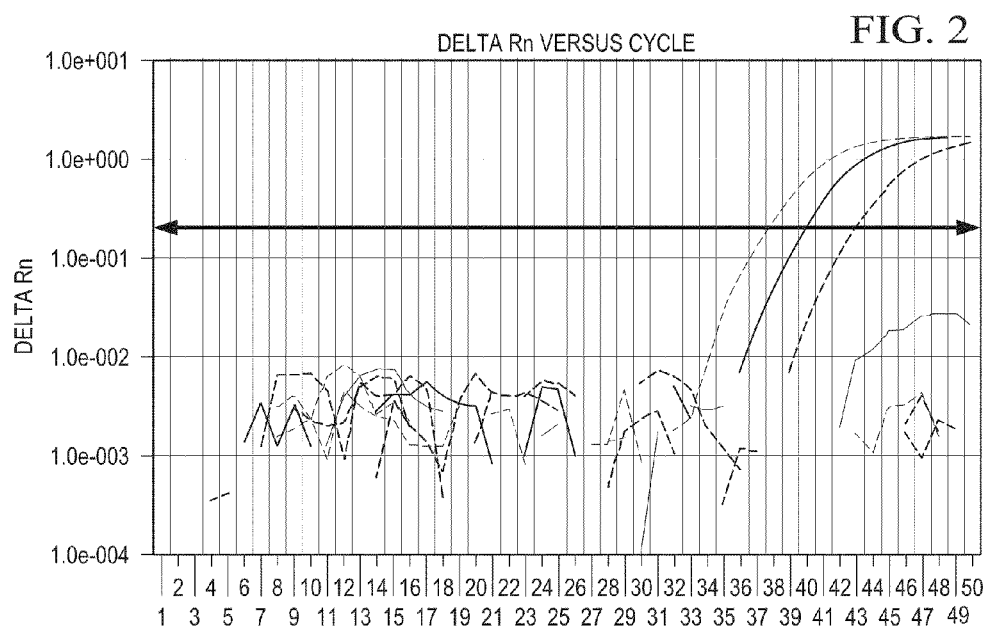
FIG. 2 shows the real time PCR data illustrating amplification of mir-29a in miRNA samples extracted using the phenol-chloroform based method (Qiagen kit) with modifications, compared with the Direct MicroRNA Analysis (DMA) approach for miRNA amplification from stool specimens of the present invention: i) The amplification profile indicated in green was generated from miRNA extracted using the Qiagen kit, ii) The two PCR profiles on the right (purple and red) were generated from direct amplification of miR29a from the stool specimens without prior miRNA extraction. The purple and red PCR profiles indicate dilution of stool samples at 1:100 and 1:1000 respectively. The jagged lines on the bottom indicate negative controls and stool samples without dilution or weaker dilutions (1:1, 1:2, and 1:10), which did not show any PCR amplification. The failed amplification in concentrated stool samples suggests the possible presence of PCR inhibitors in the stool.

FIG. 2 shows the real time PCR data illustrating amplification of mir-29a in miRNA samples extracted using the modified phenol-chloroform based method (Qiagen kit), compared with the DMA approach for miRNA amplification from stool specimens of the present invention: i) The amplification profile indicated in green was generated from miRNA extracted using the Qiagen kit and ii) The two PCR profiles on the right (purple and red) were generated from direct miRNA amplification (DMA) of miR29a from the stool specimens without prior miRNA extraction. The purple and red PCR profiles indicate dilution of stool samples at 1:100 and 1:1000 respectively. The jagged lines on the bottom indicate negative controls and stool samples without dilution or weaker dilutions (1:1, 1:2, and 1:10), which did not show any PCR amplification. The failed amplification in concentrated stool samples suggests the possible presence of PCR inhibitors in the stool. The data presented in FIG. 2 shows comparable efficiency of miRNA amplification following miRNA extraction from stool specimens using a phenol-chloroform based method or DMA.

Figure 3:
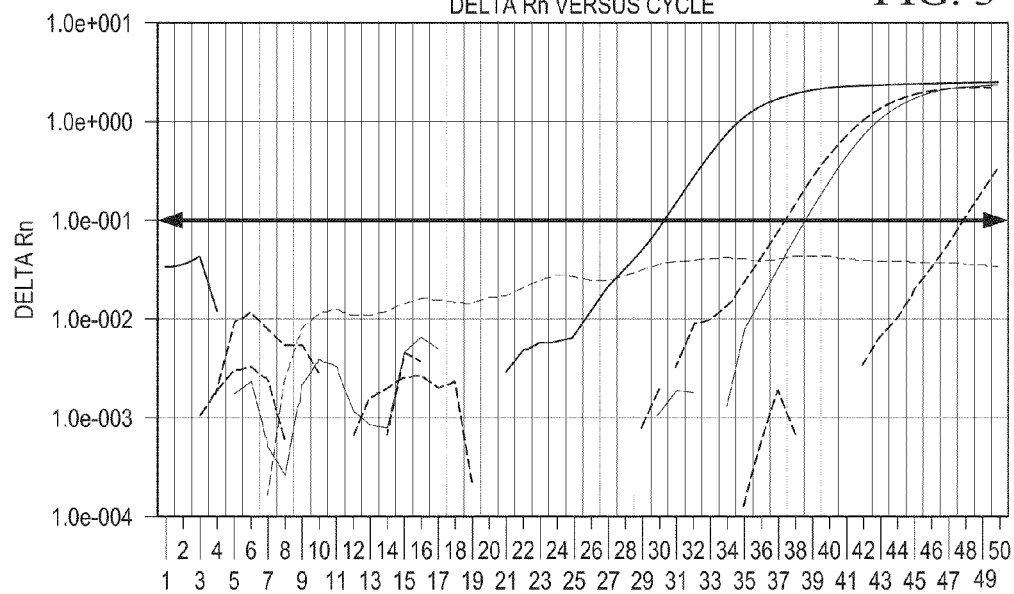
FIG. 3 shows the real time PCR for mir-29a expression in stool specimens which were either freshly collected or were stored in FOBT kits. i) The two PCR amplifications on the left (purple and red lines) indicate miR29A amplification from stool samples that were freshly collected. ii) The two PCR profiles on the right (blue and red) were generated from miRNA that was extracted from stool samples that were previously collected in FOBT kits.

FIG. 3 shows real time PCR for mir-29a expression in stool specimens which were either freshly collected or were stored in FOBT kits: (i) The two PCR amplifications on the left (purple and red lines) indicate miR29a amplification from stool samples that were freshly collected and ii) The two PCR profiles on the right (blue and red) were generated from miRNA that was extracted from stool samples that were previously collected in FOBT kits. FIG. 3 shows the robust amplification of miRNA from stool samples collected in FOBT kits.

Figure 4:
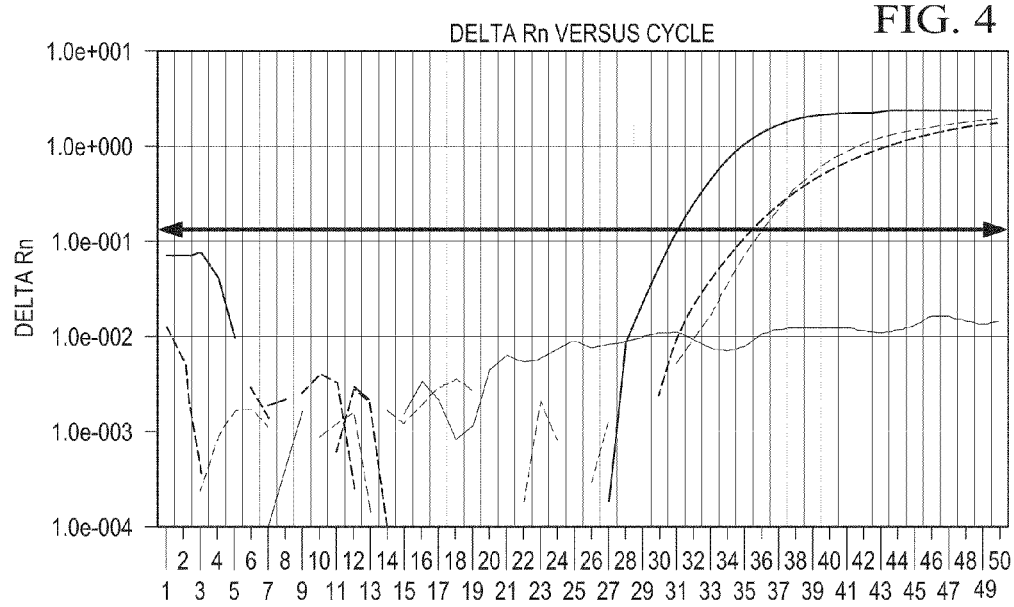
FIG. 4 shows the real time PCR data demonstrating expression of different miRNAs: The PCR amplification profiles (from left to the right) represent the expression of mir-29a, RNU6b and mir-370 respectively. A negative control is shown as a blue line on the bottom with no detectable signal.

FIG. 4 shows the real time PCR data demonstrating expression of different miRNAs: The PCR amplification profiles (from left to the right) represent the expression of mir-29a, RNU6b and mir-370 respectively. A negative control is shown as a blue line on the bottom with no detectable signal.

The data presented in FIG. 4 shows that multiple miRNAs can be amplified from stool specimens.

Figure 5A:
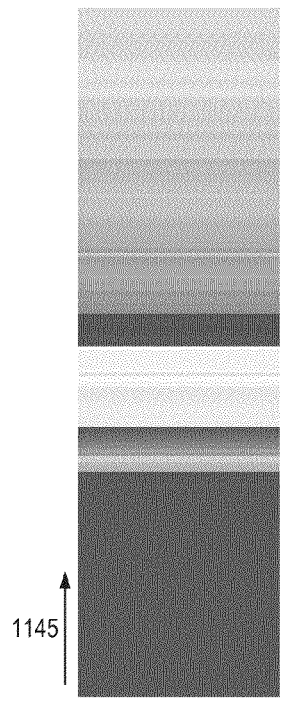
FIGS. 5A-5C show the global miRNA expression profiling from miRNA extracted from stool specimen of a healthy volunteer. Global miRNA profiling was performed on the miRNA extracted from the stool specimen of a healthy volunteer using a phenol-chloroform based method. MicroRNA profiling was performed using Illumina's miRNA expression panel with Universal Array matrix; (5A) Illumina panel of total 1145 miRNAs showing successful detection of 630 miRNAs, (5B) shows a significant detection signal. The expression levels are presented in color intensity, (5C) red—high expression and blue—no expression of miRNAs. Unsupervised clustering was performed with Gene Spring software.
Figure 5B:
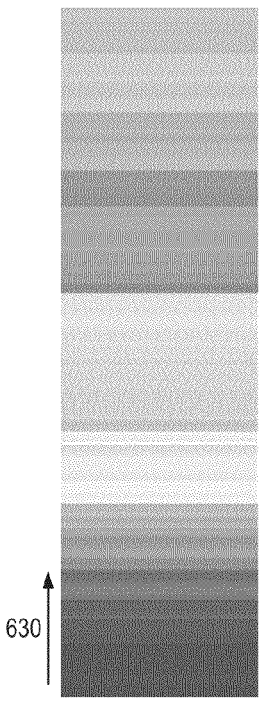
Figure 5C:
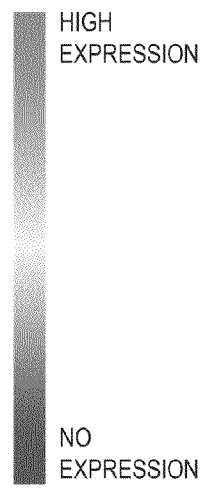

FIGS. 5A-5C show the global miRNA expression profiling from miRNA extracted from a stool specimen from a healthy volunteer. Global miRNA profiling was performed using the phenol-chloroform based method. MicroRNA profiling was performed using Illumina's miRNA expression panel with the Universal Array matrix. FIG. 5A is an Illumina panel of 1145 miRNAs showing successful detection of 630 miRNAs, FIG. 5B shows a significant detection signal. The expression levels are presented in color intensity. In FIG. 5C red indicates high expression and blue indicates no expression of miRNAs. Unsupervised clustering analysis was performed with Gene Spring software.

Figure 6A:
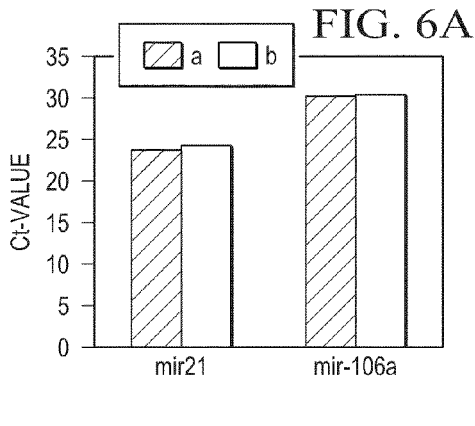
FIGS. 6A-6F shows the RT-PCR validation data of miRNA expression in stool specimens from multiple individuals using different extraction protocols. To validate the miRNA array profiling data as well as to confirm the expression pattern in other individuals we selected 2 miRNAs with different levels of miRNA expression: (6A) in line with the miRNA array data, RT-PCR analysis showed similar patterns for relative increase in expression of mir-21 and mir-106a (i.e., two specific miRNAs). The figure also illustrates the reproducibility of results in two independent miRNA extractions (shown as 'a' and 'b') from the same stool specimen, (6B) Bar graph depicting the robustness of miRNA extraction methodology as reflected in similar mir-21 and mir-106a expression levels in three independently collected stool samples (indicated as 1.1, 1.2, and 1.3) from the same healthy volunteer, (6C) Similar expression pattern of miRNA in stool from 3 independent volunteers (represented as 1, 2 and 3), (6D and 6E) show correlation of mir-21 (6D) and mir-106a (6E) expression following miRNA extraction from stool specimens by DMA or phenol-chloroform methods (mir-21: Pearson r=0.73, p=0.1, mir-106a: Pearson r=0.88, p<0.02), (6F) TaqMan RT-PCR derived Ct-values indicating a significant correlation (Pearson r=0.93, p<0.008) between mir-21 and mir-106a expression among different individuals when data were combined from all specimens shown in panels 6A, 6B and 6C.
Figure 6D:
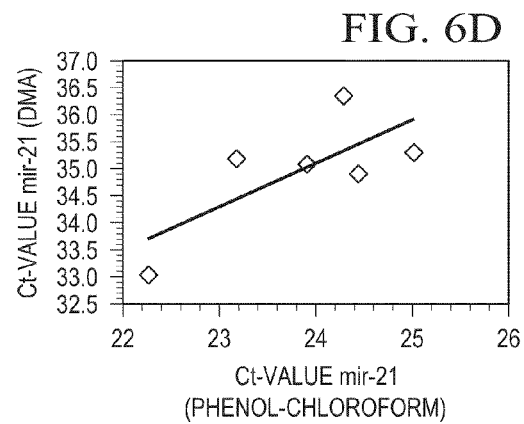
Figure 6B:
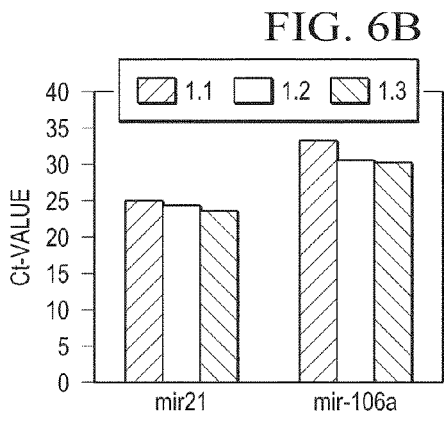
Figure 6E:
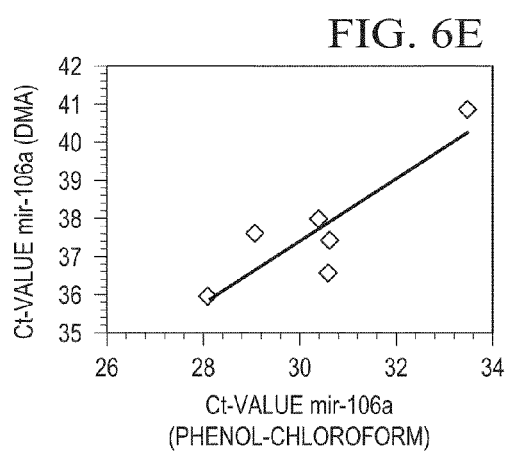
Figure 6C:
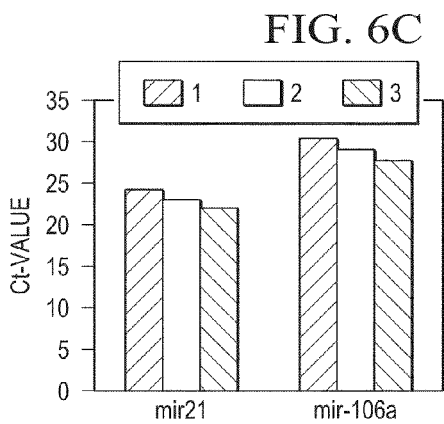
Figure 6F:
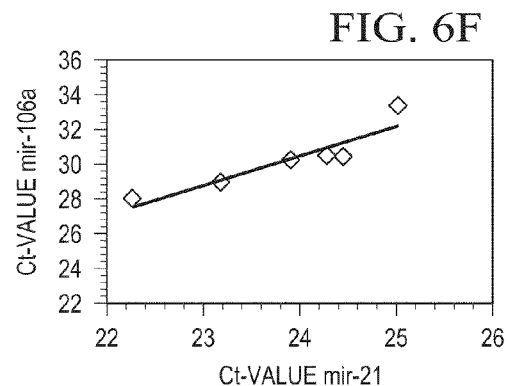

FIGS. 6A-6F show the RT-PCR validation data of miRNA expression in stool specimens from multiple individuals and using different extraction protocols. To validate the miRNA array profiling data as well as confirm the expression pattern in other individuals, the inventors selected 2 miRNAs with different levels of expression. In line with the miRNA array data, RT-PCR analysis showed similar patterns for relative increase in expression of mir-21 and mir-106a (FIG. 6A). The figure also illustrates the reproducibility of results in two independent miRNA extractions (shown as 'a' and 'b') from the same stool specimen. FIG. 6B is a bar graph depicting the robustness of miRNA extraction methodology as reflected in similar mir-21 and mir-106a expression levels in three independently collected stool samples (indicated as 1.1, 1.2 and 1.3) from the same healthy volunteer. FIG. 6C shows similar expression patterns of miRNA in stool from 3 independent volunteers (represented as 1, 2, and 3). Correlation of mir-21 (FIG. 6D) and mir-106a (FIG. 6E) expression following miRNA extraction from stool specimens by DMA or phenol-chloroform methods (mir-21: Pearson r=0.73, p=0.1, mir-106a: Pearson r=0.88, p<0.02). FIG. 6F shows TaqMan RT-PCR derived Ct-values indicating a significant correlation (Pearson r=0.93, p<0.008) between mir-21 and mir-106a expression among different individuals when data were combined from all specimens, as shown in panels 6A, 6B, and 6C.

Analysis of global miRNA expression in a stool sample from a healthy volunteer is shown in FIGS. 5A-5C show different expression patterns and intensity between miRNAs. This expression pattern or change in one or many miRNAs can be used for diagnosis, screening or even therapy of gastrointestinal diseases. The data obtained from stool samples collected from healthy volunteers is presented in Tables 3 and 4 below.

TABLE 3

Example of highly expressed miRNA detected in stool from a healthy volunteer.

| miRNA | Stool |
|---|---|
| hsa-let-7a | 14.3 |
| hsa-let-7b | 13.3 |
| hsa-let-7d | 12.3 |
| hsa-let-7f | 13.7 |
| hsa-let-7g | 14.0 |
| hsa-let-7i | 13.6 |
| hsa-miR-100 | 12.6 |
| hsa-miR-106a | 12.9 |
| hsa-miR-106b | 12.3 |
| hsa-miR-10b | 12.3 |
| hsa-miR-1184 | 12.2 |
| hsa-miR-1201 | 13.0 |
| hsa-miR-1225-5p | 12.4 |
| hsa-miR-1228 | 13.6 |
| hsa-mtR-1231 | 12.5 |

TABLE 3-continued

Example of highly expressed miRNA detected in stool from a healthy volunteer.

| miRNA | Stool |
|---|---|
| hsa-miR-1238 | 14.3 |
| hsa-miR-1246 | 14.5 |
| hsa-miR-1254 | 12.8 |
| hsa-miR-125a-5p | 13.4 |
| hsa-miR-125b | 13.2 |
| hsa-miR-126 | 12.5 |
| hsa-miR-126* | 12.6 |
| hsa-miR-1260 | 13.6 |
| hsa-miR-1274a | 14.2 |
| hsa-miR-1274b | 14.5 |
| hsa-miR-1280 | 14.4 |
| hsa-miR-1281 | 13.2 |
| hsa-miR-129-5p | 12.7 |
| hsa-miR-1300 | 12.2 |
| hsa-miR-1307 | 13.8 |
| hsa-miR-1308 | 14.1 |
| hsa-miR-130a | 12.2 |
| hsa-miR-1322 | 13.3 |
| hsa-miR-141 | 13.5 |
| hsa-miR-142-3p | 12.8 |
| hsa-miR-143 | 14.1 |
| hsa-miR-145 | 14.1 |
| hsa-miR-145* | 12.4 |
| hsa-miR-146a | 13.3 |
| hsa-miR-148a | 13.4 |
| hsa-miR-150 | 14.0 |
| hsa-miR-151-3p | 12.4 |
| hsa-miR-151-5p | 13.4 |
| hsa-miR-16 | 13.6 |
| hsa-miR-17 | 13.5 |
| hsa-miR-1826 | 14.0 |
| hsa-miR-18a | 12.2 |
| hsa-miR-191 | 13.9 |
| hsa-miR-192 | 14.2 |
| hsa-miR-193a-5p | 13.9 |
| hsa-miR-194 | 14.2 |
| hsa-miR-195 | 12.8 |
| hsa-miR-196a | 13.0 |
| hsa-miR-199a':9.1 | 13.7 |
| hsa-miR-199a-3p | 12.7 |
| hsa-miR-199a-5p | 13.5 |
| hsa-miR-199b-5p | 12.4 |
| hsa-miR-19b | 13.8 |
| hsa-miR-200a | 13.6 |
| hsa-miR-200b | 14.2 |
| hsa-miR-200b* | 12.9 |
| hsa-miR-200c | 14.2 |
| hsa-miR-202':9.1 | 12.7 |
| hsa-miR-203 | 12.0 |
| hsa-miR-20a | 14.2 |
| hsa-miR-21 | 14.8 |
| hsa-miR-214 | 12.9 |
| hsa-miR-215 | 14.3 |
| hsa-miR-22 | 12.3 |
| hsa-miR-221 | 14.0 |
| hsa-miR-223 | 14.1 |
| hsa-miR-23a | 13.9 |
| hsa-miR-23b | 13.6 |
| hsa-miR-24 | 13.7 |
| hsa-miR-25 | 13.8 |
| hsa-miR-25* | 13.4 |
| hsa-miR-26a | 13.9 |
| hsa-miR-26b | 13.6 |
| hsa-miR-27a | 13.6 |
| hsa-miR-27b | 13.3 |
| hsa-miR-28-5p | 12.7 |
| hsa-miR-29a | 13.1 |
| hsa-miR-29b | 14.0 |
| hsa-miR-29c | 13.5 |
| hsa-miR-301a | 12.1 |
| hsa-miR-302b' | 13.0 |
| hsa-miR-302d | 13.8 |
| hsa-miR-30b | 13.1 |
| hsa-miR-30c | 13.7 |
| hsa-miR-30c-1' | 13.9 |

TABLE 3-continued

Example of highly expressed miRNA detected in stool from a healthy volunteer.

| miRNA | Stool |
|---|---|
| hsa-miR-30d | 14.0 |
| hsa-miR-30e | 12.8 |
| hsa-miR-30e' | 13.4 |
| hsa-miR-31 | 13.1 |
| hsa-miR-320d | 13.5 |
| hsa-miR-335 | 13.5 |
| hsa-miR-338-3p | 12.0 |
| hsa-miR-346 | 13.1 |
| hsa-miR-374a | 13.2 |
| hsa-miR-375 | 13.9 |
| hsa-miR-423-5p | 14.0 |
| hsa-miR-425 | 12.9 |
| hsa-miR-429 | 13.7 |
| hsa-miR-451 | 13.3 |
| hsa-miR-488' | 12.1 |
| hsa-miR-504 | 14.1 |
| hsa-miR-500-5p | 12.0 |
| hsa-miR-544 | 14.7 |
| hsa-miR-550' | 12.8 |
| hsa-miR-560:9.1 | 12.7 |
| hsa-miR-584 | 12.3 |
| hsa-miR-589 | 12.6 |
| hsa-miR-594:9.1 | 13.2 |
| hsa-miR-615-3p | 12.5 |
| hsa-miR-620 | 13.8 |
| hsa-miR-622 | 13.7 |
| hsa-miR-632 | 13.3 |
| hsa-miR-650 | 14.0 |
| hsa-miR-654-3p | 13.2 |
| hsa-miR-663 | 13.4 |
| hsa-miR-671:9.1 | 12.5 |
| hsa-miR-7 | 13.1 |
| hsa-miR-7-1' | 14.4 |
| hsa-miR-720 | 14.3 |
| hsa-miR-744 | 13.1 |
| hsa-miR-768-3p | 12.9 |
| hsa-miR-768-5p | 12.9 |
| hsa-miR-874 | 12.1 |
| hsa-miR-877 | 12.6 |
| hsa-miR-885-3p | 13.1 |
| hsa-miR-890 | 12.5 |
| hsa-miR-891a | 13.4 |
| hsa-miR-923 | 14.6 |
| hsa-miR-92a | 13.7 |
| hsa-miR-92b' | 13.2 |
| hsa-miR-93 | 13.3 |
| hsa-miR-938 | 13.8 |
| hsa-miR-939 | 12.5 |
| hsa-miR-940 | 13.4 |
| hsa-miR-95 | 13.0 |
| hsa-miR-99b' | 13.8 |

Data represent miRNA with a normalized log2 signal. Unknown miRNAs were excluded from the analysis.

TABLE 4

Example of miRNA with a low or undetectable signal in the stool of healthy volunteers.

| miRNA | Stool |
|---|---|
| hsa-let-7g' | 4.1 |
| hsa-let-7i' | 2.2 |
| hsa-miR-106a:9.1 | 5.3 |
| hsa-miR-1179 | 4.2 |
| hsa-miR-1226 | 3.4 |
| hsa-miR-1228 | 6.0 |
| hsa-miR-1229 | 5.0 |
| hsa-miR-1234 | 5.8 |
| hsa-miR-124 | 4.4 |
| hsa-miR-1244 | 4.5 |
| hsa-miR-125b-2' | 4.3 |
| hsa-miR-1263 | 5.8 |
| hsa-miR-127-5p | 4.2 |
| hsa-miR-128a:9.1 | 4.1 |
| hsa-miR-128b:9.1 | 5.9 |
| hsa-miR-1296 | 5.0 |
| hsa-miR-1303 | 5.1 |
| hsa-miR-130b' | 5.9 |
| hsa-miR-135b' | 5.7 |
| hsa-miR-136 | 4.4 |
| hsa-miR-136' | 4.1 |
| hsa-miR-133-1' | 5.6 |
| hsa-miR-141' | 3.6 |
| hsa-miR-144' | 4.5 |
| hsa-miR-147 | 4.2 |
| hsa-miR-148a' | 5.2 |
| hsa-miR-149 | 4.5 |
| hsa-miR-149' | 5.9 |
| hsa-miR-150' hsa- | 6.0 |
| hsa-miR-153 | 5.7 |
| hsa-miR-154' | 5.4 |
| hsa-miR-156' | 5.2 |
| hsa-miR-16-2' | 4.7 |
| hsa-miR-1825 | 5.5 |
| hsa-miR-187 | 5.1 |
| hsa-miR-190b | 4.9 |
| hsa-miR-191' | 5.6 |
| hsa-miR-192' | 5.5 |
| hsa-miR-200c' | 3.0 |
| hsa-miR-202' | 5.3 |
| hsa-miR-20a' | 3.7 |
| hsa-miR-212 | 4.3 |
| hsa-miR-218-2' | 4.5 |
| hsa-miR-220b | 6.0 |
| hsa-miR-220c | 5.7 |
| hsa-miR-221' | 3.5 |
| hsa-miR-26a-1' | 4.1 |
| hsa-miR-26b' | 4.6 |
| hsa-miR-29a' | 5.6 |
| hsa-miR-29b-2' | 3.1 |
| hsa-miR-302b | 6.0 |
| hsa-miR-302c' | 5.9 |
| hsa-miR-30a' | 3.8 |
| hsa-miR-323-3p | 4.8 |
| hsa-miR-324-5p | 5.7 |
| hsa-miR-329 | 5.5 |
| hsa-miR-337-3p | 5.7 |
| hsa-miR-337-5p | 5.9 |
| hsa-miR-338-5p | 4.9 |
| hsa-miR-340 | 5.2 |
| hsa-miR-340' | 5.6 |
| hsa-miR-342-5p | 5.5 |
| hsa-miR-345 | 4.4 |
| hsa-miR-34a' | 5.1 |
| hsa-miR-34b | 3.4 |
| hsa-miR-34c-3p | 4.8 |
| hsa-miR-361-3p | 4.9 |
| hsa-miR-362-5p | 4.4 |
| hsa-miR-370 | 5.8 |
| hsa-miR-374b' | 5.3 |
| hsa-miR-376a' | 4.1 |
| hsa-miR-379' | 5.0 |
| hsa-miR-364 | 5.4 |
| hsa-miR-409-5p | 5.1 |
| hsa-miR-410 | 5.1 |
| hsa-miR-411 | 4.0 |
| hsa-miR-412 | 5.7 |
| hsa-miR-433 | 5.8 |
| hsa-miR-449a | 5.1 |
| hsa-miR-454' | 5.4 |
| hsa-miR-487a | 5.7 |
| hsa-miR-468 | 4.9 |
| hsa-miR-490-5p | 5.3 |
| hsa-miR-494 | 5.4 |
| hsa-miR-496 | 5.3 |
| hsa-miR-501-5p | 3.5 |
| hsa-miR-502-3p | 5.6 |

TABLE 4-continued

Example of miRNA with a low or undetectable signal in the stool of healthy volunteers.

| miRNA | Stool |
|---|---|
| hsa-miR-505 | 5.0 |
| hsa-miR-505' | 4.3 |
| hsa-miR-511 | 5.8 |
| hsa-miR-512-3p | 5.7 |
| hsa-miR-517' | 5.5 |
| hsa-miR-515a-5p | 6.0 |
| hsa-miR-518f | 3.8 |
| hsa-miR-519a | 4.9 |
| hsa-miR-519d | 5.3 |
| hsa-miR-519e' | 4.3 |
| hsa-miR-525-3p | 5.6 |
| hsa-miR-542-5p | 4.8 |
| hsa-miR-543 | 5.7 |
| hsa-miR-545 | 4.9 |
| hsa-miR-545' | 5.3 |
| hsa-miR-548d-3p | 4.2 |
| hsa-miR-548d-5p | 5.6 |
| hsa-miR-548e | 3.6 |
| hsa-miR-548j | 5.6 |
| hsa-miR-548l | 5.9 |
| hsa-miR-546o | 4.8 |
| hsa-miR-550 | 5.8 |
| hsa-miR-551b | 4.7 |
| hsa-miR-553 | 4.7 |
| hsa-miR-556-3p | 3.7 |
| hsa-miR-579 | 4.8 |
| hsa-miR-582-3p | 4.4 |
| hsa-miR-590-3p | 5.4 |
| hsa-miR-598 | 5.6 |
| hsa-miR-602 | 5.9 |
| hsa-miR-616' | 4.6 |
| hsa-miR-629 | 5.1 |
| hsa-miR-629' | 4.7 |
| hsa-miR-641 | 5.9 |
| hsa-miR-653:9.1 | 5.3 |
| hsa-miR-655 | 5.7 |
| hsa-miR-656 | 4.8 |
| hsa-miR-657 | 5.8 |
| hsa-miR-659 | 5.8 |
| hsa-miR-706' | 6.0 |
| hsa-miR-7-2' | 5.0 |
| hsa-miR-760 | 4.5 |
| hsa-miR-765 | 5.0 |
| hsa-miR-769-3p | 5.1 |
| hsa-miR-801:9.1 | 5.3 |
| hsa-miR-877' | 4.0 |
| hsa-miR-885-5p | 5.7 |
| hsa-miR-892a | 4.7 |
| hsa-miR-935 | 4.9 |
| hsa-miR-941 | 3.7 |

Data represent miRNA with a normalized log2 signal. Unknown miRNAs were excluded from the analysis.

TABLE 5

Efficiency of each gene in real-time PCR process.

| gene | efficiency | avg Ct | min Ct | max Ct | IQR |
|---|---|---|---|---|---|
| mir-21 | 2 | 25.25 | 22.05 | 31.48 | 2.5 |
| mir-17 | 2 | 28.88 | 25.58 | 33.22 | 1.28 |
| mir-143 | 2 | 34.31 | 30.03 | 40.17 | 3.72 |
| mir-622 | 2 | 35.16 | 31.47 | 41.06 | 1.89 |
| mir-654-3p | 2 | 35.19 | 31.45 | 39.66 | 2.43 |
| mir-16 | 2 | 30.27 | 26.43 | 35.17 | 2.19 |
| mir-26b | 2 | 34.05 | 31.18 | 39.92 | 1.72 |
| mir-106a | 2 | 32.24 | 27.82 | 36.6 | 1.77 |

The present invention discloses the feasibility of fecal miRNAs as potential biomarkers for detecting colorectal neoplasia. An ideal biomarker must fulfill several criteria including, the potential to be measured quantitatively, high degree of specificity that indicates aberration in a specific biological and/or pathogenic process, reliability, measurability, sensitivity, and predicatability. Studies by the present inventors indicate that miRNAs are abundantly present in stool and can be easily and reproducibly detected in stool specimens. Furthermore, the observation that intra-individual miRNA expression patterns were relatively constant, highlights the potential significance of miRNA as a screening tool. After determining the feasibility of detecting miRNA expression in fecal materials, the present inventors studied whether the fecal miRNA profiles from healthy subjects were similar to the ones present in normal colonic mucosal epithelium. Interestingly, but not surprisingly the inventors found differences in miRNA expression patterns between stool and colonic mucosa specimens. This is in line with the previous reports, where similar observations were made for miRNA profiling in blood and cancer tissues (18, 23). The fact that we could easily detect miRNAs in stool using the novel DMA methodology, suggests that miRNA-biomarkers in stool are contributed both via cell exfoliation and by the accumulation of exosomes in the gastrointestinal tract, as previously suggested for the presence of miRNA signatures in blood (24-26).

In order to evaluate the potential of fecal miRNAs as biomarkers for detecting colorectal neoplasia, the inventors performed a pilot analysis on a small collection of the clinical samples. Although a blood-based test might seem more practical, considering the increased number of exfoliated colortocytes shed in the colon from CRC patients compared to healthy subjects, it is highly likely that the earliest detectable neoplastic changes in the expression pattern of specific miRNAs may be in feces rather than in blood, (12, 27). The selection of miRNAs was based on the either a previously published role of these specific miRNAs, or based on unpublished data obtained following miRNA expression profiling in CRCs and normal mucosa tissues by the present inventors. Early premalignant adenomas as well as early stage cancers are the ideal targets for a CRC prevention strategy. Previous few studies on miRNA-based non-invasive biomarkers have mainly focused on the CRC patients only, and no data exist on miRNA-based biomarkers for the identification of patients with colonic adenomas. In this pilot study the inventors analyzed patients from both groups—with colonic adenomas and CRC. Interestingly, the observation for the higher expression of miR-21 and -106a in colonic neoplasia compared to subjects with normal colonoscopy, is very encouraging, and is in agreement with results previously reported for this miRNA in adenoma and CRC tissues (6).

The present invention effectively extracts miRNA from stool with high reproducibility using a commercially available kit and a modified method. No correlation was observed between stool total RNA concentration and expression of currently used normalizers (RNU6b, mir-26b or mir-16). Due to high RNU6b degradation we used mir-16 and -26b as an internal normalizer that showed significant correlation in expression to each other but not to RNU6b. Comparison of independent extraction shows high reproducibility of miRNAs expression. miRNA expression profile between stool and normal colonic mucosa tissue shows both similarities and differences. MiRNA expression in stool samples collected at different time points of healthy volunteers show similar expression patterns especially in miRNAs that are highly present in feces. Similar to that, miRNA analysis in different healthy volunteers shows similarities in expression patterns. Further, the present inventors effectively extracted miRNA from fecal occult blood test kits. Using FOBT samples from 29 patients who underwent CRC screening with colonoscopy the inventors found significantly higher expressions of mir-21 and mir106a.

In summary, the present invention demonstrates an easy, effective, and reproducible extraction technique for miRNAs from freshly collected, as well as from FOBT stool samples. Differential expression of miRNA in stool of patients with colorectal neoplasia suggests that fecal miRNAs may serve as potential biomarkers. Fecal miRNAs may provide a novel, promising, and non-invasive approach for diagnosis of early colorectal neoplasia.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations or the listed items preceding the term. For example, "A, B, C, or combinations thereof" is intended to include at least one of A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,252,955: *Method of Defecting Colon Cancer*.

U.S. Pat. No. 6,645,730: *Noninvasive Demotion of Colorectal Cancer and other Gastrointestinal Pathology*.

U.S. Pat. No. 6,586,177: *Methods for Disease Detection*.

(1) Jemal A, Siegel R, Ward E, Murray T, Xu J, Thun M J. Cancer Statistics, 2007. CA Cancer J Clin 2007;57:43-66.

(2) Jankowski J A, Odze R D. Biomarkers in Gastroenterology: Between Hope and Hype comes Histopathology. Am J Gastroenterol 2009;104:1093-096.

(3) Meissner H I, Breen N, Klabunde C N, Vernon S W. Patterns of Colorectal Cancer Screening Uptake Among Men and Women in the United States. Cancer Epidemiol Biomarkers Prev 2006;15:389-94.

(4) Ouyang D L, Chen J J, Getzenberg R H, Schoen R E. Noninvasive Testing for Colorectal Cancer: A Review. Am J Gastroenterol 2005;100:1393-403.

(5) Imperiale T F, Ransohoff D F, Itzkowitz S H, Turnbull B A, Ross M E. Fecal DNA versus Fecal Occult Blood for Colorectal-Cancer Screening in an Average-Risk Population. N Engl J Med 2004;351:2704-714.

(6) Schetter A J, Leung S Y, Sohn J J, Zanetti K A, Bowman E D, Yanaihara N, et al. Microna Expression Profiles Associated with Prognosis and Therapeutic Outcome in Colon Adenocarcinoma. JAMA 2008;299:425-36.

(7) Levine J S, Abnen D J. Clinical practice. Adenomatous Polyps of the Colon. N Engl J Med 2006;355(24):2551-7.

(8) Graser A, Stieber P, Nagel D, et al. Comparison of CT Colonography, Colonoscopy, Sigmoidoscopy and Faecal Occult Blood Tests for the Detection of Advanced Adenoma in an Average Risk Population. Gut 2009;58(2):241-8.

(9) Mandel J S, Bond J H, Church T R, et al. Reducing Mortality from Colorectal Cancer by Screening for Fecal Occult Blood. Minnesota Colon Cancer Control Study. N Engl J Med 1993;328(19):1365-71.

(10) Lieberman D A. Clinical practice. Screening for Colorectal Cancer. N Engl J Med 2009;361(12):1179-87.

(11) Zou H, Taylor W R, Harrington J J, et al. High Detection Rates of Colorectal Neoplasia by Stool DNA Testing with A Novel Digital Melt Curve Assay. Gastroenterology 2009;136(2):459-70.

(12) Nagasaka T, Tanaka N, Cullings H M, et al. Analysis of Fecal DNA Methylation to Detect Gastrointestinal Neoplasia. J Natl Cancer Inst 2009;101(18):1244-58.

(13) Ambros V. The Functions of Animal microRNAs. Nature 2004;431(7006):350-5.

(14) Lu J, Getz G, Miska E A, et al. MicroRNA Expression Profiles Classify Human Cancers. Nature 2005;435(7043):834-8.

(15) Calin G A, Croce C M, MicroRNA Signatures in Human Cancers. Nat Rev Cancer 2006;6(11):857-66.

(16) Hui A B, Shi W, Boutros P C, et al. Robust Global Micro-RNA Profiling with Formalin-Fixed Paraffin-Embedded Breast Cancer Tissues. Lab Invest 2009;89(5):597-606.

(17) Mitchell P S, Parkin R K, Kroh E M, et al. Circulating microRNAs as Stable Blood-Based Markers for Cancer Detection. Proc. Natl Acad Sci U S A 2008;105(30):10513-8.

(18) Chen X, Ba Y, Ma L, et al. Characterization of microRNAs in Serum: A Novel Class of Biomarkers for Diagnosis of Cancer and other Diseases. Cell Res 2008;18(10):997-1006.

(19) Cortez M A, Calin G A. MicroRNA Identification in Plasma and Serum: A New Tool to Diagnose and Monitor Diseases. Expert Opin Biol Ther 2009;9(6):703-11.

(20) Chen C, Ridzon D A, Broomer A J, et al. Real-time Quantification of microRNAs by Stem-Loop RT-PCR. Nucleic Acids Res 2005;33(20):e179.

(21) Vandesompele J, De P K, Pattyn F, et al. Accurate Normalization of Real-time Quantitative RT-PCR Data by Geometric Averaging of Multiple Internal Control Genes. Genome Biol 2002;3(7):RESEARCH0034.

(22) Mestdagh P, Van V P, De W A, et al. A Novel and Universal Method for microRNA RT-qPCR Data Normalization. Genome Biol 2009;10(6):R64.

(23) Ng E K, Chong W W, Jin H, et al. Differential Expression of Micromas in Plasma of Patients with Colorectal Cancer: A Potential Marker for Colorectal Cancer Screening. Gut 2009;58(10):1375-81.

(24) Hunter M P, Ismail N, Zhang X, et al. Detection of microRNA Expression in Human Peripheral Blood Microvesicles. PLoS One 2008;3(11):e3694.

(25) Chan J A, Krichevsky A M, Kosik K S. MicroRNA-21 is an Antiapoptotic Factor in Human Glioblastoma Cells. Cancer Res 2005;65(14):;6029-33.

(26) Rabinowits G, Gercel-Taylor C, Day J M, Taylor D D, Kloecker G H. Exosomal microRNA: A Diagnostic Marker for Lung Cancer. Clin Lung Cancer 2009;10(1):42-6.

(27) Deschner E E. Early Proliferative Changes in Gastrointestinal Neoplasia. Am J Gastroenterol 1982;77(4):207-11.

(28) Du P, Kibbe W A, Lin S M. Lumi: A Pipeline for Processing Illumina Microarray. Bioinformatics 2008;24(13):1547-8.

What is claimed is:

1. A method of processing a biological sample comprising ribonucleic acids of a subject for characterization of one or more target MicroRNAs (miRNAs) in the sample comprising the steps of:
   a) mixing the sample with RNase free water, a salt solution, or both to form a suspension;
   b) centrifuging the suspension;
   c) separating an miRNA-containing supernatant from the centrifuged suspension;
   d) amplifying the one or more miRNAs without prior RNA extraction;
   wherein the sample containing ribonucleic acid is mixed with RNase free water, a salt solution, or both without a prior extraction.

2. The method of claim 1, wherein the biological sample contains miRNA in exosomes.

3. The method of claim 1, wherein the biological sample is a stool sample.

4. The method of claim 1, wherein the salt is an ionic salt selected from the group consisting of sodium salts, potassium salts, calcium salts, magnesium salts, ammonium salts, iron salts, and quarternary ammonium salts.

5. The method of claim 1, wherein a ratio of the biological sample to the salt solution is selected from the group consisting of 1:1, 1:2, 1:5, 1:10, 1:20, 1:25, 1:50, and 1:100.

6. The method of claim 5, wherein the salt solution is a sodium chloride solution.

7. The method of claim 1, further comprising storing the supernatant at −80.degree. C. following step c).

8. The method of claim 1, further comprising measuring a total RNA/microRNA (miRNA) concentration in the supernatant using a spectrophotometer before amplification.

9. The method of claim 1, wherein the amplifying of the miRNA comprises transcribing a cDNA from the RNA-containing supernatant using one or more specific miRNA primers; amplifying the transcribed cDNA using a polymerase chain reaction assay to obtain one or more amplified miRNAs.

10. The method of claim 9, wherein the specific miRNA primers are specific for miR-21.

11. The method of claim 9, wherein the specific miRNA primers are specific for miR-106a.

12. The method of claim 9, wherein said characterization of one or more target miRNAs aids in detecting a disease in a subject suspected of having the disease, said method further comprising comparing the levels of the one or more miRNAs from the sample containing ribonucleic acid of the subject suspected of having the disease with that of one or more healthy subjects, and wherein an elevated level of the one or more miRNAs indicates the presence of the disease.

13. The method of claim 12, wherein the disease is a cancer.

14. The method of claim 12, wherein the disease is a gastroenterological disease.

15. The method of claim 12, wherein the disease is colorectal or gastroenterological cancer.

16. The method of claim 12, wherein the disease is colon adenoma, colon adenocarcinoma, or colorectal cancer.

17. The method of claim 12, wherein endoscopic examination of the subject is carried out if and only if the one or more miRNAs indicating presence of the disease is elevated.

18. The method of claim 12, wherein if the one or more miRNAs indicating the presence of the disease is elevated, then the method further comprises endoscopic removal of polyps and/or adenomas from the subject.

19. The method of claim 12, wherein the target miRNA is miR-21.

20. The method of claim 15, wherein the target miRNA is miR-21.

21. The method of claim 1, wherein the biological sample is a blood sample.

* * * * *